(12) United States Patent
Herzenberg et al.

(10) Patent No.: US 10,452,746 B2
(45) Date of Patent: Oct. 22, 2019

(54) QUANTITATIVE COMPARISON OF SAMPLE POPULATIONS USING EARTH MOVER'S DISTANCE

(75) Inventors: Leonore A. Herzenberg, Stanford, CA (US); Guenther Walther, Stanford, CA (US); Wayne A. Moore, San Francisco, CA (US); Noah Zimmerman, Palo Alto, CA (US)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 390 days.

(21) Appl. No.: 13/342,722

(22) Filed: Jan. 3, 2012

(65) Prior Publication Data
US 2012/0173199 A1 Jul. 5, 2012

Related U.S. Application Data

(60) Provisional application No. 61/429,355, filed on Jan. 3, 2011.

(51) Int. Cl.
*G06F 17/18* (2006.01)
(52) U.S. Cl.
CPC .................................. *G06F 17/18* (2013.01)
(58) Field of Classification Search
CPC ................ G01N 15/1429; G06F 15/00; G06F 17/30247; G06F 17/30244; G06F 17/18; G06F 17/30705; G06F 19/3443; G06F 17/30256
USPC ........................................................ 702/181
See application file for complete search history.

(56) References Cited

U.S. PATENT DOCUMENTS

| 8,473,215 B2 | 6/2013 | Walther et al. | |
| 2005/0246105 A1* | 11/2005 | Faber | G01N 33/5026 702/19 |
| 2006/0020597 A1* | 1/2006 | Keating | G06F 17/3025 |
| (Continued) | | | |

OTHER PUBLICATIONS

Rubner et al., "A Metric for Distributions with Applications to Image Databases", Jan. 1998, IEEE, 59-66.*
(Continued)

*Primary Examiner* — Mohamed Charioui
*Assistant Examiner* — Eyob Hagos
(74) *Attorney, Agent, or Firm* — McCarter & English, LLP; Beverly W. Lubit

(57) ABSTRACT

A method and apparatus for quantitatively measuring differences between portions of a multivariate, multi-dimensional sample distribution, may comprise summarizing the data by dividing the data into clusters each having a signature representative of a position of the cluster and a fraction of the entire distribution within the cluster; matching a plurality of first supplier signatures to a respective one of a plurality of second receiver signatures using a cost factor indicative of the separation between first signature elements and second signature elements; and determining a measurement of the work required to transform the first signature to the second signature. The step of determining a measurement of the work may comprise applying the earth mover distance ("EMD") algorithm between the first signature or elements of the first signature and the respective second signatures or elements of the respective second signature.

39 Claims, 9 Drawing Sheets

(56) References Cited

U.S. PATENT DOCUMENTS

| | | | |
|---|---|---|---|
| 2006/0263829 A1* | 11/2006 | Evans | C12N 5/0612 435/7.2 |
| 2007/0118297 A1 | 5/2007 | Thayer | |
| 2008/0243398 A1 | 10/2008 | Rabinowitz et al. | |
| 2009/0204637 A1* | 8/2009 | Li | G06F 17/3025 |
| 2010/0112628 A1 | 5/2010 | Gernez et al. | |
| 2010/0204973 A1* | 8/2010 | Parkinson | C12Q 1/6883 703/11 |
| 2013/0226469 A1* | 8/2013 | Robinson | G06F 15/00 702/27 |

OTHER PUBLICATIONS

Rubner et al., "The Earth Mover's Distance, Multi-Dimensional Scaling, and Color-Based Image Retrieval," DARPA IUW, 1997, all pages.*

Guibas et al., the earth mover's distance, multi-dimensional scaling, and colour based image retrieval, 1997, IEEE, p. 1-8.*

Levina et al., The Earth Mover's Distance is the Mallows Distance: Some Insights from Statistics, 2001, IEEE.*

Roederer, M. et al. "Probability binning comparison: a metric for quantitating univariate distribution differences", Cytometry. 2001; vol. 45(1), pp. 37-46. (Need this).

Bagwell, C. "A journey through flow cytometric immunofluorescence analyses—Finding accurate and robust algorithms that estimate positive fraction distributions", Clin. Immunol. Newsletter. 1996; pp. 33-37 (Need this).

Hitchcock, F. L. "The distribution of a product from several sources to numerous localities", J Math. Phys. 1941; vol. 20, 224-230 (Need this).

Gentleman, R. et al. "Bioconductor: open software development for computational biology and bioinformatics", Genome Biology. 2004; vol. 5(10), pp. 1-16.

Murphy, R. F. et al., "Automated identification of subpopulations in flow cytometric list mode data using cluster analysis", Cytometry. 1985; vol. 6(4), pp. 302-309.

Bakker, T. C. et al., "Cluster analysis of flow cytometric list mode data on a personal computer", Cytometry. 1993; vol. 14(6), pp. 649-659.

Demers, S. et al. "Analyzing multivariate flow cytometric data in aquatic sciences", Cytometry. 1992; vol. 13(3), pp. 291-298.

Boedigheimer, M. J. et al. "Mixture modeling approach to flow cytometry data", Cytometry. 2008; vol. 73(5), pp. 421-429.

Lo, K. et al. "Automated gating of flow cytometry data via robust model-based clustering", Cytometry. 2008; vol. 73(4), pp. 321-332.

Walther, G. et al. "Automatic clustering of flow cytometry data with density-based merging", Adv Bioinformatics. 2009, pp. 1-7.

Finch, P.D. et al. "Substantive difference and the analysis of histograms from very large samples", J Histochem Cytochem. 1979; vol. 27(3), pp. 800.

Young, I.T. "Proof without prejudice: use of the Kolmogorov-Smirnov test for the analysis of histograms from flow systems and other sources", J Histochem Cytochem. 1977; vol. 25(7), pp. 935-941.

Overton, W.R. "Modified histogram subtraction technique for analysis of flow cytometry data", Cytometry. 1988; vol. 9(6), pp. 619-626.

Lampariello, F. "Evaluation of the number of positive cells from flow cytometric immunoassays by mathematical modeling of cellular autofluorescence", Cytometry. 1994; vol. 15(4), pp. 294-301.

Rogers, W.T. et al., "FlowFP: A Bioconductor Package for Fingerprinting Flow Cytometric Data", Adv Bioinformatics. 2009; vol. 2009, pp. 1-11.

Rubner, Y. et al., "A metric for distributions with applications to image databases", Proceedings of the 1998 IEEE International Conference on Computer vision. 1998, pp. 59-66.

Levina, E. et al., "The earth mover's distance is the mallows distance:some insights from statistics", 2001, IEEE, all pages.

Rubner, Y. et al., "The earth mover's distance, multi-dimensional scaling and color-based image retrieval", DARPA IUW, 1997, all pages.

Godtliebsen, F. et al., "Significance in scale space for bivariate density estimation", 1999, pp. 1-18.

Lampariello, F. et al., "Complete mathematical modeling method for the analysis of immunofluorescence distributions composed of negative and weakly positive cells", Cytometry.1998; vol. 32, pp. 241-254.

Fan, Jianqing and Marron, James S. "Fast implementations of nonparametric curve estimators". Journal of Computational and Graphical Statistics. 1994, vol. 3,35-56.

* cited by examiner

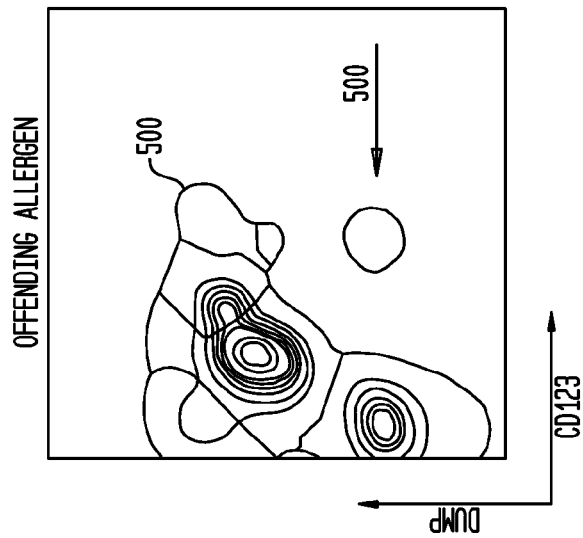
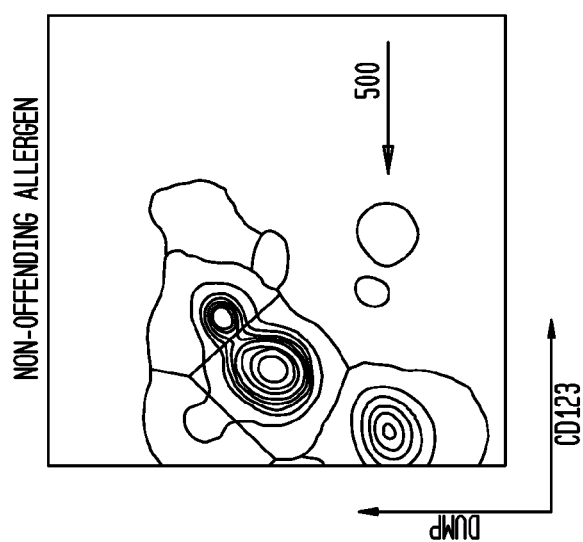
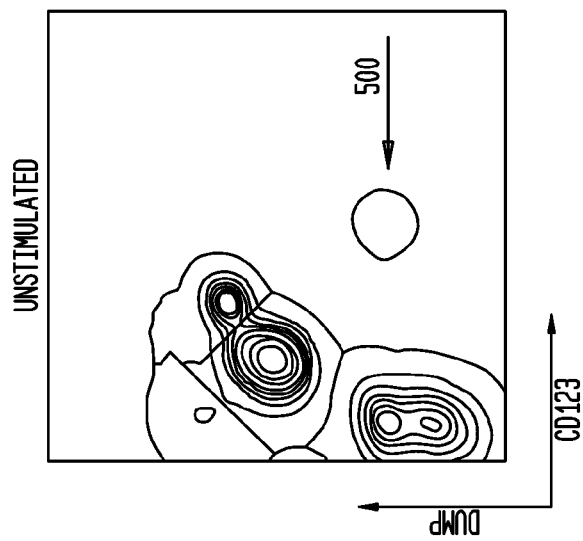

QUANTITATIVE COMPARISON OF SAMPLE POPULATIONS USING EARTH MOVER'S DISTANCE

CROSS REFERENCE TO RELATED APPLICATIONS

This application claims the benefit of priority to U.S. Provisional Application No. 61/429,355 (filed on Jan. 3, 2011) entitled "QUANTITATIVE COMPARISON OF SAMPLE POPULATIONS USING EARTH MOVER'S DISTANCE," the content of which is incorporated herein in its entirety.

STATEMENT OF GOVERNMENT FUNDING

This invention was made with Government support under contract LM007033 awarded by the National Institutes of Health. The government has certain rights in this invention.

FIELD OF THE INVENTION

This invention relates to methods of analyzing data from high-dimensional multi-sample experiments, such as with the use of flow cytometry.

BACKGROUND

Populations of sample data having multivariate distributions, which, e.g., have no known normalized distribution shape, can be very hard to analyze. Flow cytometry allows to measure simultaneously multiple characteristics of thousands of cells. This ability has made flow cytometry a prevalent instrument in both the research and clinical settings. However, the full potential of this technology is limited by the lack of data analysis methodology and software that allows for an automated and objective analysis of the data generated by flow cytometry instruments. While the disclosed subject matter is explained generally in the context of analyzing flow cytometry data, as noted, there is a much broader application than flow cytometry, including any large distribution of multivariate data, such as census data, data regarding which stores and products shoppers at a shopping mall are attracted to on a given day or in a given time period, and the like.

One important part of the analysis of flow cytometry data is gating, i.e., the identification of homogenous subpopulations of cells. The current standard technique for this type of analysis is to draw 2D gates manually with a mouse on a computer screen, based on the user's interpretation of density contour lines that are provided by software tools such as FlowJo (at treestar.com) or BioConductor (Gentleman, R., et al. Genome Biology, 5:R80, 2004). The cells falling in this gate are extracted and the process is repeated for different 2D projections of the gated cells, thus resulting in a sequence of two-dimensional gates that describe subpopulations of the multivariate flow cytometry data.

There are several obvious problems with this kind of analysis. The analysis is subjective since it is based on the user's interpretation and experience, error prone, difficult to reproduce, time consuming, and does not scale to a high-throughput setting. Accordingly, manual gating has become a major limiting aspect of flow cytometery, and there is a widely recognized need for more advanced analysis techniques.

There have been several attempts to produce automatic and objective gates. These methods employ the k-means algorithm (Murphy, R. F., Cytometry, 6(4):302-309, 1985; Bakker, T. C., et al. Cytometry, 14(6):649-659, 1993; Demers, S., et al., Cytometry, 13(3):291-298, 1992) or mixture models with Gaussian components (Boedigheimer, M. J., and Ferbas, J., Cytometry A, 73(5):421-429, 2008) or with t components and a Box-Cox transformation (Lo, K., et al. Cytometry A, 73(4):321-322, 2008). A commonly shared limitation of these methods is that they produce necessarily convex subpopulations; whereas occasionally subpopulations occur that are not convex and are, for example, kidney shaped. Such subpopulations can arise, for example, when two markers are added sequentially, so that there is a developmental progression over time that moves the subpopulation first in one direction and then in another direction.

Density-Based Merging

Density-based merging (DBM) is grounded in nonparametric statistical theory which allows for such subpopulations. DBM follows the paradigm that clusters of the data can be delineated by the contours of high-density regions; this also is the rationale that underlies manual gating. The paradigm is implemented algorithmically (Walther, G., et al., Advances in Bioinformatics, Vol. 2009, Article ID: 686759) by constructing a grid with associated weights that are derived by binning the data. This grid provides for a fast computation density estimated via the Fast Fourier Transform, and it provides for an economical but flexible representation of clusters. Each high-density region is modeled by a collection of grid points (Walther, G., et al., Advances in Bioinformatics, Vol. 2009, Article ID: 686759). This collection is determined as follows: 1) links are established between certain neighboring grid points based on statistical decisions regarding the gradient density estimate. The aim is to connect neighboring grid points by a chain of links that follow the density surface "uphill." The result is a number of chains that link certain grid points and which either terminate at the mode of a cluster or represent background that will not be assigned to a cluster; 2) the algorithm then will combine some of these chains if statistical procedures indicate that they represent the same cluster. The end result of the algorithm results in clusters that are represented by chains that link certain grid points. This representation provides an efficient data structure for visualizing and extracting the cells that belong to a cluster (Walther, G., et al., Advances in Bioinformatics, Vol. 2009, Article ID: 686759). The chains that link grid points in a cluster represent a tree structure which can be traversed backwards to efficiently enumerate all grid points in the cluster and hence to retrieve all cells in the cluster via their nearest neighbor grid point. Software implementation of DBM can allow for automatic 2D gating that is based on statistical theory and provide the information necessary to decide on the number of populations in the sample (Walther, G., et al., Advances in Bioinformatics, Vol. 2009, Article ID: 686759).

Probability Binning Comparison

Probability binning comparison of univariate distributions utilizes a variant of the chi-squared statistic (Roederer, M., et al. Cytometry, 45:37-46, 2001). In this variant, a control distribution is divided such that an equal number of events fall into each of the divisions, or bins. This approach minimizes the maximum expected variance for the control distribution and can be considered a mini-max algorithm. The control-derived bins then are applied to test sample distributions, and a normalized chi-squared value is computed (Roederer, M., et al. Cytometry, 45:37-46, 2001). While several algorithms for the comparison of univariate distributions arising from flow cytometry analyses have been developed and studied, algorithms for comparing multivariate distributions remain elusive. For example, algorithms, such as Kolmogorov-Smirnoff (K-S) statistics (Finch, P. D., J. Histochem. Cytochem. 27:800, 1979; Young, I. T., J. Histochem. Cytochem. 25:935-941, 1977), Overton subtraction (Overton, W. R., Cytometry, 9:619-626, 1988), SED (Bagwell, C., Clin. Immunol. Newsletter, 16:33-37, 1996), and some parametric models (Lampariello, F., Cytometry, 15:394-301, 1994; Lampariello, F., and Aiello, A., Cytometry, 32:241-254, 1998) are limited to univariate data. These types of algorithms commonly are utilized for their ability to determine whether or not given distributions are (statistically significantly) different, and/or to determine the fraction of events that are positive compared to a control distribution.

Univariate tools generally are sufficient with 3- or 4-parameter data (due to the relative independence of the measurements), however, they generally are never sufficient when the number of parameters is greater than five or six. Data analysis becomes significantly more difficult since the complexity of the data (and the analysis) increases geometrically with the number of parameters; these difficulties are becoming more apparent as the utilization of six or more color analysis becomes more routine, (i.e., 8+ parameter data).

Probability binning comparison also provides a useful metric for determining the probability with which two or more multivariate distributions represent distinct sets of data (Roederer, M., et al. Cytometry, 45:47-55, 2001). The metric can be used to identify the similarity or dissimilarity of samples. In this approach, hyper rectangles of n dimensions (where n is the number of measurements being compared) comprise the bins used for the chi-squared statistic. These hyper-dimensional bins are constructed such that the control sample has the same number of events in each bin; the bins are then applied to the test samples for chi-squared calculations (Roederer, M., et al. Cytometry, 45:47-55, 2001).

Fundamentally, the multivariate PB algorithm is identical to the univariate PB algorithm. The unique aspect of the multivariate algorithm is how the data is divided into bins on which the comparison is performed. As for the univariate comparison, the algorithm chosen results in a binning that equally divides the control distribution, i.e., any single event from the control distribution, selected at random, has the same probability of falling into any of the given bins.

Fingerprinting Multivariate Probability Distribution Function of Flow Cytometery Data The flow FP algorithm ("fingerprinting", "FlowFP") utilizes the PB algorithm to subdivide multivariate space into hyperrectangular regions that contain nearly equal numbers of events (Rogers, W. T. and Holyst, H. A., Advances in Bioinformatics, Vol. 2009, Article ID: 193947). The algorithm determines regions (bins) by (1) finding the variable (meaning parameter as used in the context of flow cytometry) whose variance is highest, (2) dividing the population at the median of this variable which results in two bins, each with half of the events, and (3) repeating this process for each subset in turn. At the first level of binning the population is divided into two bins; at the second level, each of the two "parent" bins is divided into two "daughter" bins, and so forth. The final number of bins n is determined by the number of level 1 of recursive subdivision, such that $n=2^l$.

Initially, the binning procedure can be performed for a collection of samples (instances), called a "training set." The result of the process models the structure of the multivariate space occupied by the training set by the way it constructs bins of varying size and shape; this is referred to as a "model" of the space (not to be confused with modeling approaches that fit data to a parameterized model or set of models). Then, the model is applied to another set of samples (which may or may not include instances from the training set). This operation results in a feature vector of event counts in each bin of the model for each instance in the set. These feature vectors are, in the context of a specific model, a unique description of the multivariate probability distribution function for each instance in the set of samples, and thus are referred to as "fingerprints" ("FP").

Each element of a fingerprint represents the number of events in a particular subregion of the model (Rogers, W. T., and Holyst, H. A., Advances in Bioinformatics, Vol. 2009, Article ID: 193947). It is possible to determine which of these regions are informative with respect to an experimental question by using appropriate statistical tests, along with corrections for multiple comparisons, to ascertain which regions (if any) are differentially populated in two or more groups of samples. If the number of events in a bin is regarded as one of n features describing an instance, then the statistical determination of informative subregions is seen to be a feature selection procedure.

Fingerprint features are useful in two distinct modes: 1) all or a selected subset of features can be used in clustering or classification approaches to predict the class of an instance based on its similarity to groups of instances, and 2) the events within selected, highly informative bins can be visualized within their broader multivariate context in order to interpret the output of the modeling process.

However, there are limitations to fingerprinting of flow cytometry data. For example, fingerprinting approaches are sensitive to differences in multivariate probability distributions no matter their origin, i.e., instrumental, reagent, or other systematic variations may cause spurious signals as large or larger than true biological effects. Further, fingerprinting responds to factors that might artificially emphasize certain bins in preference to others. For example, events may pile up on either the zero or full-scale axis for one or more variables. This can result from values that would be negative due to compensation or background subtraction (causing pileup on the zero axis) or, conversely, from values that exceed the dynamic range of the signal detection apparatus (causing pileup at full scale). In both situations, this falsely results in a apparent high density of events. A distortion in the proper characterization of the true multivariate probability distribution function results as FP bins are "attracted" to these locations. Additionally, scaling and transformation remain important for FP. Data acquired using linear amplifiers (found in some modern instruments), or data that have been "linearized" from instruments with logarithmic amplifiers, tend to be heavily skewed to the left, since in most cases data distributions are quasi-log-normally distributed. Accordingly, bins determined from linearized data have extreme variations in size. Generally, a good rule of thumb is to use a data transformation that produces the most spread out distribution; this also is often the transformation most effective for clear visualization of the distribution.

Fingerprinting also is limited by the number of events available for analysis. The objective of probability binning is to find bins containing equal numbers of events. Once the number of bins is on the order of the number of events in an instance, the expected number of events per bin will be of order unity; the differences in bin counts will not be statistically significant. Conversely, if the dimensionality of the data set is high, the average number of times any variable will be divided in the binning process will be small. Thus, the spatial resolution of binning is limited by the number of events collected, and as the number of variables increases, the number of events needed to maintain resolution increases geometrically.

Earth Mover's Distance

Histogram-based local descriptors are ubiquitous tools in numerous computer vision tasks, such as shape matching, image retrieval, texture analysis, color analysis, and 3D object recognition. For comparing these descriptors, it is common to apply bin-to-bin distance functions, including $L_p$ distance, $\chi^2$ statistics, KL divergence, and Jensen-Shannon (JS) divergence. In applying these bin-to-bin functions, it is often assumed that the domain of the histograms are previously aligned. However, in practice, such an assumption can be violated due to various factors, such as shape deformation, non-linear lighting change, and heavy noise. The Earth Mover's Distance (EMD) is a cross-bin distance function that addresses this alignment problem. EMD defines the distance between two histograms as the solution of the transportation problem that is a special case of linear programming (LP). In addition to color and texture signature applications, EMD is useful for more general classes of histogram descriptors such as SIFT and shape context. Despite this favorable robustness property, EMD has seldom been applied to general histogram-based descriptors (especially local descriptors). The main reason lies in its expensive computational cost, which is larger than $O(N^3)$ (super-cubic[1]) for a histogram with N bins.

Since its initial proposal by Rubner et al., EMD has attracted a large amount of research interest. Cohen and Guibas studied the problem of computing a transformation between distributions with minimum EMD. Levina and Bickel proved that EMD is equivalent to the Mallows distance when applied to probability distributions. Tan and Ngo applied EMD for common pattern discovery using EMD's partial matching ability. Indyk and Thaper proposed a fast approximation EMD algorithm and used it for image retrieval and shape matching. In addition, Holmes et al. touched on several areas explored in the paper, including EMD approximations in a Euclidean space for classes of derivative histograms and partial matching.

Accordingly, there remains a need for data analysis methodology and software that allows for an automated and objective analysis of the data

SUMMARY

A method and apparatus for quantitatively measuring the difference between portions of a multivariate, multi-dimensional sample distribution, may comprise the steps of: summarizing the data by dividing the data into clusters each having a signature representative of a position of the cluster and a fraction of the entire distribution within the cluster; matching a plurality of first supplier signatures to a respective one of a plurality of second receiver signatures using a cost factor indicative of the separation between the first signature or elements of the first signature and the second signature or elements of the second signature; and determining a measurement of the work required to transform the first signature to the second signature. The step of determining a measurement of the work may comprise applying the earth mover distance ("EMD") algorithm between the first signature or elements of the first signature and the respective second signatures or elements of the respective second signature.

The first supplier signature may a plurality of clusters each comprising a cluster location representative and a cluster weight; and the second receiver signature may comprise a plurality of clusters each comprising a cluster location representative and a cluster weight. The first supplier signature may comprise a plurality of M clusters and the second receiver signature comprising a plurality of N clusters. The determining of a measurement of the work required step may comprise: determining a separation distance matrix D between a first supplier cluster matrix element and a second receiver cluster matrix element; determining a flow F between first supplier cluster matrix element and the second receiver cluster matrix element that minimizes the overall costs; and, using the flow F to find the work to transform the plurality of first supplier clusters into the plurality of second receiver clusters.

The method may comprise: normalizing the work to the total optimized flow F. The apparatus may be a programmed computer, a computer program on a storage medium or a sample distribution analyzer.

BRIEF DESCRIPTION OF THE DRAWINGS

FIG. 12A shows distributions of data in the form sample populations illustrating aspects of an embodiment of the disclosed subject matter;

FIG. 12B shows distributions of data in the form sample populations illustrating aspects of an embodiment of the disclosed subject matter;

FIG. 12 C illustrates the mapping of clusters to the same cluster in different sample populations for different patients or for differing tests;

DETAILED DESCRIPTION

Glossary

Figure 1:
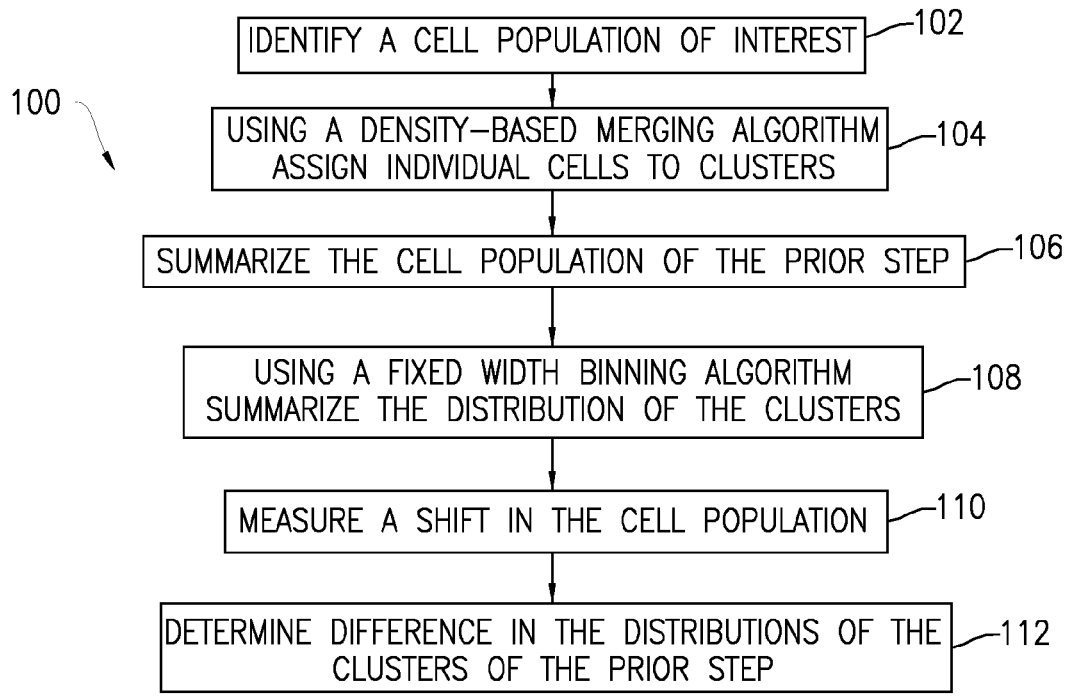
FIG. 1 shows in block diagram form the steps in a method for quantitative measurement of the difference in multi-dimensional sample distributions, such as flow cytometry samples, according to aspects of an embodiment of the disclosed subject matter.

The term "binning" as used herein refers to a process of grouping measured data into data classes. These data classes can be further used in various analyses.

The term "centroid" (geometric center) as used herein refers to the intersection of all straight lines that divide a shape into two parts of equal moment about the line. The geometric centroid of a convex object always lie in the object. A non-convex object might have a centroid that is outside the figure itself. The centroid of a ring or a bowl, for example, lies in the object's central void. If the centroid is defined, it is a fixed point of all isometries in its symmetry group. In particular, the geometric centroid of an object lies in the intersection of all its hyperplanes of symmetry. The centroid of many figures (for example, but not limited to, a regular polygon, a regular polyhedron, a cylinder, a rectangle, a rhombus, a circle, a sphere, a ellipse, a ellipsoid, a superellipse, a superellipsoid) can be determined by this principle alone. In particular, the centroid of a parallelogram is the meeting point of its two diagonals. This is not true for other quadrilaterals. For the same reason, the centroid of an object with translational symmetry is undefined (or lies outside the enclosing space), because a translation has no fixed point.

The term "ChiSq value" as used herein refers to unnormalized values that are proportional to actual chi-square values and are calculated from the deviations of the measured event from the fit line in each of the spectral overlap fluorescences.

The term "compensation" as used herein refers to correction of an emission signal to accurately estimate the fluorescence signal for a given fluorophore.

The term "cytometry" as used herein refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and to collect cells (or other small particles) with measured characteristics that fall within a user-selected range of values.

The term "Earth Mover's Distance" (EMD) refers to a metric for measuring the difference between two multivariate distributions.

The term "Fast Fourier Transform" ("FFT") refers to an efficient algorithm to compute the discrete Fourier transform (DFT) and its inverse. There are many distinct FFT algorithms involving a wide range of mathematics, from simple complex-number arithmetic to group theory and number theory. A DFT is a specific kind of Fourier transform, used in Fourier analysis. A DFT decomposes a sequence of values into components of different frequencies.

The term "fluorescence" as used herein refers to the result of a three-state process that occurs in certain molecules, generally referred to as "fluorophores" or "fluorescent dyes," when a molecule or nanostructure relaxes to its ground state after being electrically excited. Stage 1 involves the excitation of a fluorophore through the absorption of light energy; Stage 2 involves a transient excited lifetime with some loss of energy; and Stage 3 involves the return of the fluorophore to its ground state accompanied by the emission of light.

The term "fluorescent-activated cell sorting" (also referred to as "FACS"), as used herein refers to a method for sorting a heterogeneous mixture of biological cells into one or more containers, one cell at a time, based upon the specific light scattering and fluorescent characteristics of each cell.

The term "gating" as used herein refers to the identification of homogenous subpopulations of cells. The current standard technique during the analysis of flow cytometry data is to draw 2D gates manually with a mouse on a computer screen, based on the user's interpretation of density contour lines that are provided by software tools such as, for example, but not limited to, FlowJo (at treestar.com) of BioConductor. The cells falling in this gate are extracted and the process is repeated for different 2D projections of the gated cells, thus resulting in a sequence of two-dimensional gates that described subpopulations of the multivariate flow cytometry data.

The term "parameter" as used herein refers to a reference, value, or variable that refers to one of the pieces of data provided as input to a function, procedure, protocol, command, or program.

The term "reagent" as used herein refers to a substance used in a chemical reaction to detect, measure, examine, or produce other substances. Reagents include, but are not limited to, a dye, an antibody, a fluorophores, and a chromophore.

The term "stain" as used herein refers to a composition of a dye(s) or pigment(s) used to make a structure, a material, a cell, a cell component, a membrane, a granule, a nucleus, a cell surface receptor, a peptide, a microorganism, a nucleic acid, a protein or a tissue distinguishable. The term "staining reagent" and, unless otherwise defined, the term "reagent" as used herein are synonymous with the term "stain."

The term "stain set" as used herein refers to a combination of stains. The terms "reagent combination" and "multiparameter stain set" as used herein are synonymous with the term "stain set." The term "marker" as used herein refers to a structure that is associated with a cell or particle and is detectable because it emits a signal including, but not limited to, fluorescence, that can be measured by a detection instrument or because it is reactive with a reagent that emits such a signal or causes the emission of such a signal.

The term "single stained" control or single stained sample as used herein refers to cells or particles whose fluorescence derives from a single stain, reagent, dye, or pigment.

The "unstained control" as used herein refers to cells or particles that are not known to have fluorescence derived from a stain, reagent, dye, or pigment.

Unless defined otherwise, all technical terms used herein have the same meaning as commonly understood by one of skill in the art to which this disclosed subject matter belongs. Any methods and materials similar or equivalent to those described herein also can be used in the practice of or testing utilizing of the presently disclosed subject matter.

It must be noted that as used herein and in the appended claims, the singular forms "a", "and", and "the" include plural references unless the context clearly dictates otherwise.

Reference in the present specification to "one embodiment" or "an embodiment" means that a particular feature, structure, or characteristic described in connection with the embodiment is included in at least one embodiment of the invention. The appearances of the phrase "in one embodiment" or "an embodiment" in various places in the specification do not necessarily all refer to the same embodiment.

According to aspects of the disclosed subject matter described herein the subject matter is in part described with reference to block diagrams and operational illustrations of methods and devices and devices implementing methods to qualitatively and quantitatively analyze distributions of data, e.g., populations of sample results, in multidimensional spaces. It is understood that each block of the block diagrams or operational illustrations, and combinations of blocks in the block diagrams or operational illustrations, can be implemented by means of analog or digital hardware and computer program instructions or combinations thereof.

These computer program instructions can be provided to a processor of a general purpose computer, special purpose computer, microcontroller, ASIC, or any other programmable data processing apparatus (a "computing device"), such that the instructions, which execute via the processor of the computing device or other programmable data processing apparatus, implement the functions/acts specified in the block diagrams or operational block or blocks.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved. In addition different blocks may be implemented by different processors, such as an array or processors operating in series or parallel arrangement, and exchanging data and/or sharing common data storage media.

For the purposes of this disclosure, a non-transitory computer readable medium stores computer programs and/or data in machine readable form. By way of example, and not limitation, a computer readable medium can comprise computer storage media and communication media. Computer storage media includes volatile and non-volatile, removable and non-removable media implemented in any method or technology for storage of information such as computer-readable instructions, data structures, program modules, specific applications or other data.

Method for Quantitative Comparison of Flow Cytometry Samples

Turning now to FIG. 1, according to one aspect of the disclosed subject matter, there is shown in block diagram form steps in a method 100 for quantitative comparison of multivariate distributions of sample populations, such as flow cytometry samples, the method 100 comprising steps:

a) identifying a population of interest, such as a cell population, as represented in block 102:

wherein a merging algorithm, such as a density-based merging algorithm can be used, e.g., to assign individual cells to a respective cluster, e.g., based on at least two measurements, as represented in block 104;

b) summarizing the cell population of step (a), as represented in block 106:

wherein a binning algorithm, such as a fixed width binning algorithm, may be used, e.g., to summarize the distribution of the clusters assembled in step (a), as represented in block 108; and c) measuring a shift in the population, such as a cell population, as represented in block 110:

wherein the difference in the distributions of the clusters of step (b) is determined, as represented in block 112.

1. Identifying Cell Population of Interest

Figure 2:
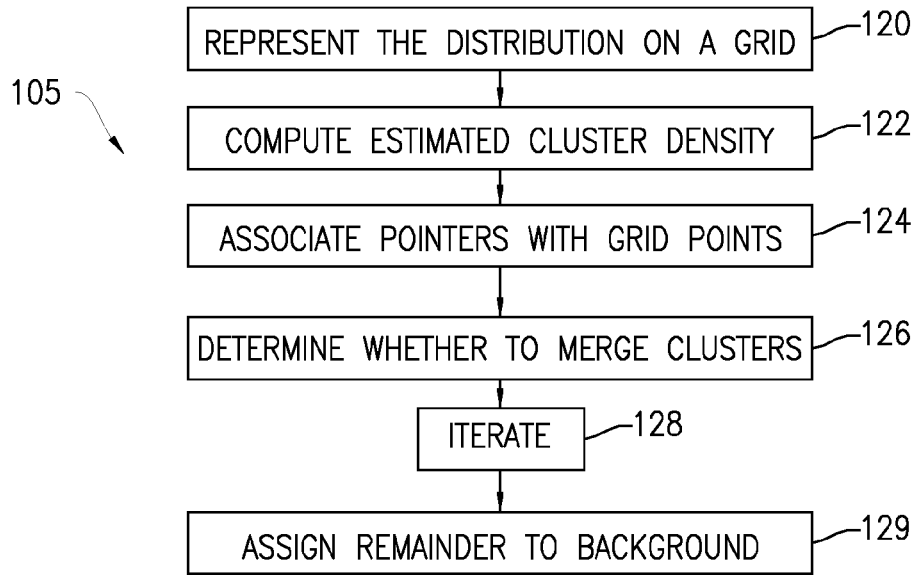
FIG. 2 shows in block diagram form the steps of a method for performing two of the steps in the method of FIG. 1.

Turning now to FIG. 2, according to a possible embodiment, there is shown in block diagram form a method 105 comprising the steps for performing the identifying step of block 102 and the assigning step of block 104 of FIG. 1, wherein a merging algorithm, such as a density-based merging method can be used, e.g., to assign individual cells to a respective cluster, e.g., based on at least two measurements, wherein the density-based merging method comprises the steps of:

(1) representing the distribution on a grid, as indicated in block 130. A software implementation of this methodology can work with successive 2D projections and can be described in this setting (although the algorithm can be generalized to work in higher dimensions from the start). Thus, n data points $x_i=(x_{i1},x_{i2})$, $i=1,\ldots n$, can be selected, as also illustrated in block 130. To construct a grid, a positive integer M, typically M=128 or 256, is chosen, and a grid can then be constructed consisting of $M^2$ points as follows. Set $\Delta_j=(\max_i x_{i,j}-\min_i x_{i,j})/(M-1)$, $j=1,2$, and define the jth coordinate $y(_{m1,m2})$ to be to be $y_{mj}=\min_i x_{i,j}+(m_j-1)\Delta_j$, $m_j=1,\ldots,M$. Then the grid is defined as $\{y(_{m1,m2}):(m_1,m_2) \in \{1,\ldots,M\}^2\}$, all as illustrated in block 132.

Next, as illustrated in block 134, each grid point $y_m$, where $m=(m_1,m_2)\in\{1,\ldots,M\}^2$, is assigned a weight $w_m$ by linearly binning the observations $x_i$, that is $$w_m = \sum_{i=1}^{n}\prod_{j=1}^{2} \max\left(0, 1 - \frac{|x_{i,j} - y_{mj}|}{\Delta_j}\right).$$

The grid $\{y_m, m\in\{1,\ldots,M\}^2\}$ and the associated weights $\{w_m, m\in\{1,\ldots,M\}^2\}$ represent an approximation to the cell distribution. The software implementation can allow the user to choose various values of M. A larger choice of M results in a finer grid and hence a more precise approximation of the cell distribution at the expense of more computing time. A relatively small number of bins can give an excellent approximation. Within a precision of 0.01% of the total cell population, a change in the outcome of gating small populations when increasing M from the default value of 256 to 512 is mostly undetectible.

Figure 4:
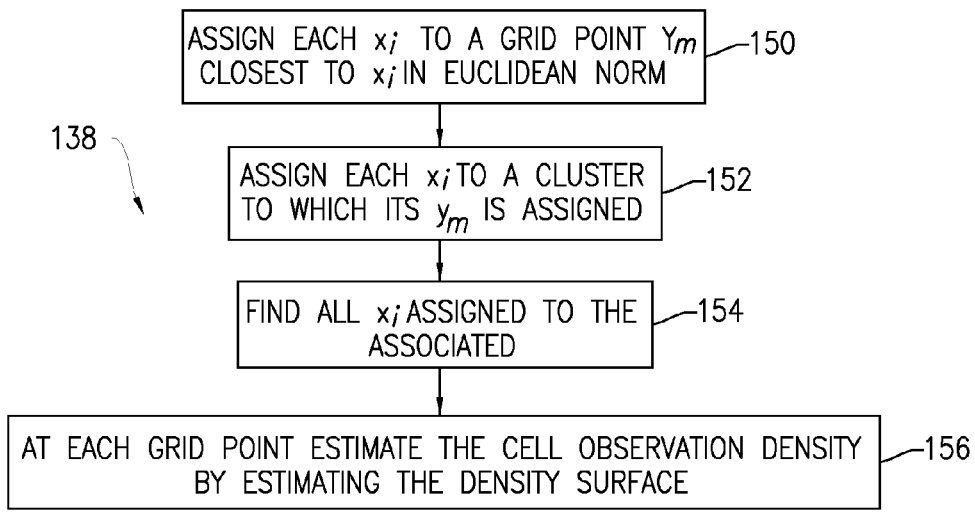
FIG. 4 shows in block diagram form the steps of a method for performing one of the steps in the method of FIG. 3.

A clustering algorithm using only the grid and the associated weights can be used to derive the clustering assignment, as indicated in block 136. This assignment is then applied to cluster observations $x_i$ as follows, as illustrated in block 138 and further detailed with respect to FIG. 4. Each observation $x_i$ is assigned to the grind point $y_m$ that is the closest to $x_i$ in Euclidean norm as represented in block 150. Then, as illustrated by block 152, $x_i$ is assigned to the same cluster to which its associated grid point $y_m$ is assigned to the given cluster. As indicated by block 154 the method may include the step of finding all observations $x_i$ that are assigned to these grid points, thereby clustering the observations, as illustrated by block 138.

According to aspects of an embodiment of the claimed subject matter the computing the estimate of the cell density step of block 122 can be accomplished as follows. At each grid point $y_m$, $m\in\{1,\ldots,M\}^2$, an estimate of the density surface $\hat{f}(y_m)$ can be computed as follows:

Denote by $\phi(x)=1/\sqrt{2\pi} \exp(-x^2/2)$ the Gaussian kernel. Then the estimated density at $y_m$ is given by $$\hat{f}(y_m) = \frac{1}{n}\sum_{l_1=-Z_1}^{Z_1}\sum_{l_2=-Z_2}^{Z_2} w_{m-1} \times \prod_{j=1}^{2} \frac{\phi(l_j\Delta_j/h_j)}{h_j},$$

where $l=(l_1,l_2)$, $Z_j=\min([4h_j/\Delta_j], M-1)$, and $h_j=SD(\{x_{i,j}, i=1,\ldots,n\})n^{-1/6}$, where SD denotes standard deviation. The above sum can be computed quickly with the Fast Fourier Transform (FFT) as known, or using the above formula without the FFT.

According to aspects of an embodiment of the disclosed subject matter the association step of block 124 can be used to make an association of pointers between the grid points. First, for each grid point, the standard error of the corresponding density estimate can be computed, then those grid points whose density does not pass a certain statistical threshold can be labeled as background, as indicated by block 158. The interpretation of this criterion is that it tests whether the density is significantly different from zero as discussed above.

Next, according to block 160 links between grid points that follow the density gradient (i.e., point "uphill") are constructed. To this end, each grid point is visited in turn and the density estimate on this grid point compared with those of its neighboring grid points, of which there are at most eight. A link to that neighboring grid point that has the highest value of the density estimate is established, as indicated by block 162, provided that the difference in density estimates is statistically significant. Testing whether the latter difference is nonzero may be necessary as otherwise the variability of the density estimate may lead to links that may accidently connect different clusters. Computationally links are implemented by way of the programming language data type of a pointer.

Figure 3:
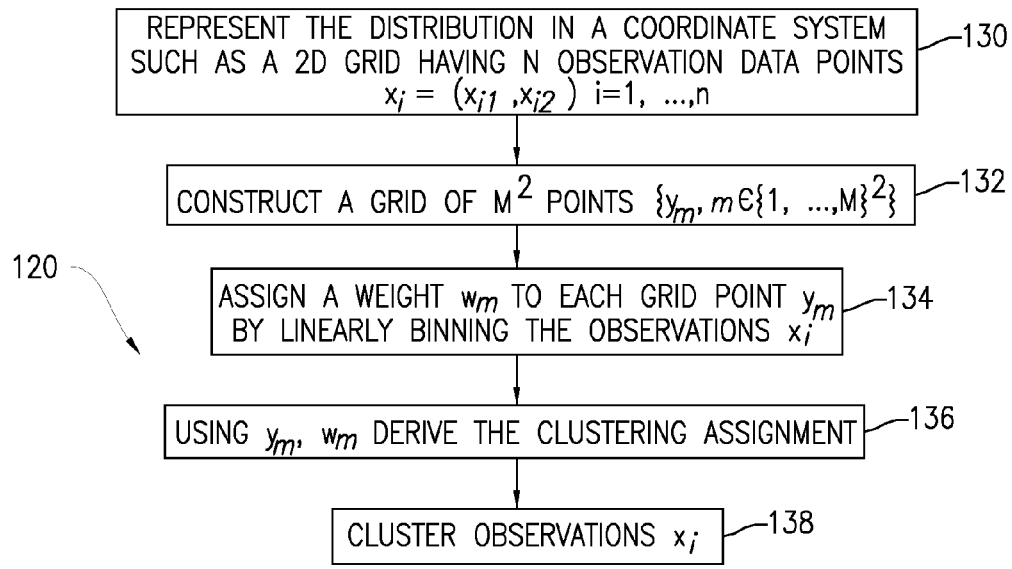
FIG. 3 shows in block diagram form the steps of a method for performing one of the steps in the method of FIG. 2.
Figure 5:
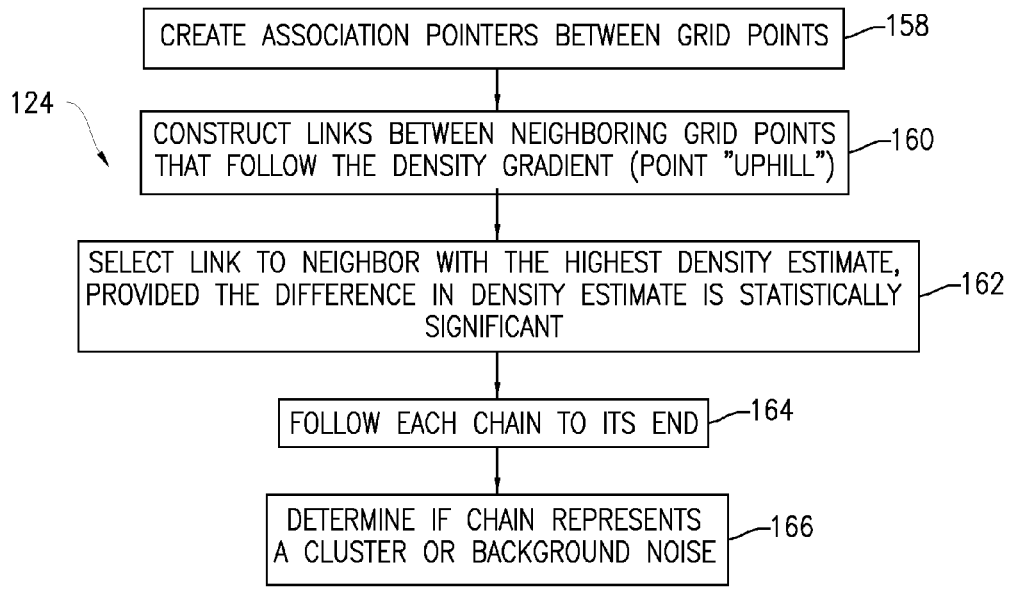
FIG. 5 shows in block diagram form the steps of a method for performing one of the steps in the method of FIG. 2.
Figure 6:
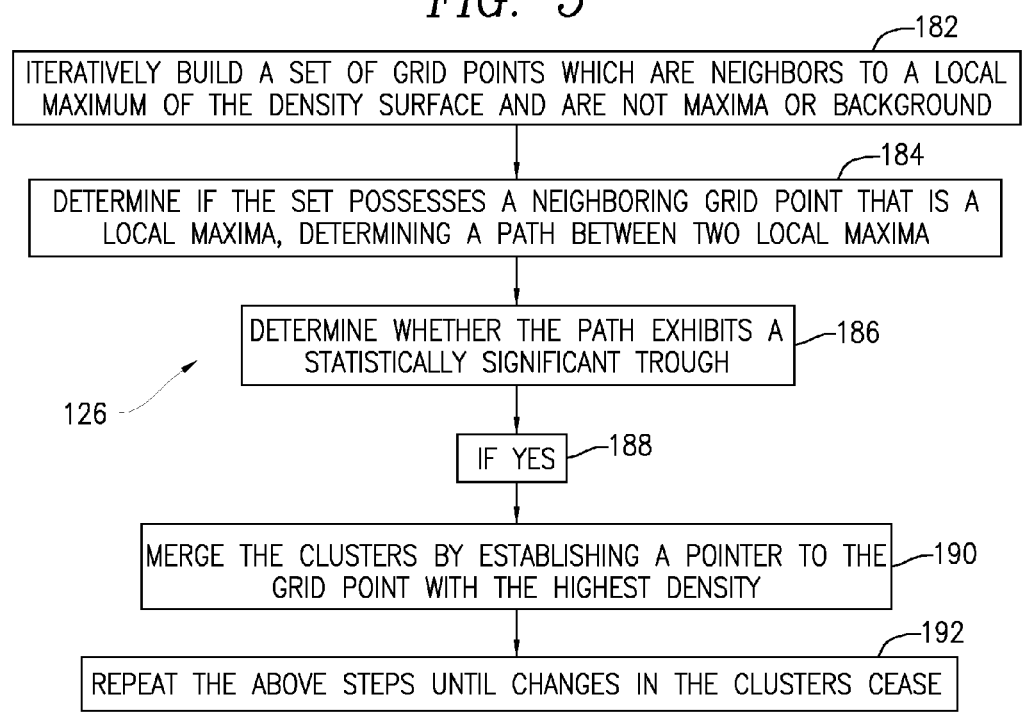
FIG. 6 shows in block diagram form the steps of a method for performing one of the steps of the method of FIG. 2.

Next, each chain is followed to its end as indicated in block 164 and it is determined whether it represents a cluster or background, as indicated in block 166. Then, it is determined whether two clusters need to be merged because they are connected by a path that possesses no statistically significant trough, block 186, as illustrated in more detail in FIG. 5. This is done by iteratively building a set of grid points which are neighbors to a local maximum of the density surface, are not maxima or background, as illustrated by block 182 in FIG. 6, and which are determined not to exhibit a statistically significant change in density when compared to the local maximum, block 184. If this set in turn possesses a neighboring grid point that is a local maximum, then a path has been found (via this set) between two local maxima, block 184 that does not exhibit a statistically significant trough block 188. Consequently, the last part of the step of block 126 merges the corresponding clusters by establishing pointers to the grid point with the highest density, block 190. The steps of FIG. 6, as indicated in block 192 may be iterated until there are no more changes in the clusters. It can be shown that there will be only finitely many iterations. The step of block 129 can then take care of the remaining points that can be assigned to the background. Thus the resulting number of clusters can be determined by the data via the statistical methodology described above. Further description of these steps is as follows:

Regarding the step of block 122, described in more detail in FIG. 3, consider all grid points $y_m$, $m \in \{1,\ldots,M\}^2$, in turn. For each grid point $y_m$ according to aspects of an embodiment of the disclosed apparatus and method, it may compute $$\hat{\sigma}_m^2 = \frac{1}{n(n-1)} \sum_{l_1=-Z_1}^{Z_1} \sum_{l_2=-Z_2}^{Z_2} w_{m-l} \times \prod_{j=1}^{2} \frac{\phi^2(l_j\Delta_j/h_j)}{h_j^2} - \frac{1}{n-1}\hat{f}(y_m)^2.$$

$\hat{\sigma}$ is an estimate of the standard error of the estimated density at $y_m$.

$\hat{\sigma}_m^2$ can be computed with the FFT as above. Define the index set $$\mathcal{S} = \{m \in \{1,\ldots,M\}^2 : \hat{f}(y_m) > 4.3 * \sqrt{\hat{\sigma}_m^2}\}.$$

The factor 4.3 is an adjustment for multiple testing over the grid and may easily be obtained (see, for example, by Godtliebsen, F., et al., Significance in scale space for bivariate density estimation. *Journal of Computational and Graphical Statistics*, 11(1):1-21, 2002).

$\mathcal{S}$ is the set of grid points, where the density is significantly different from zero. Grid points outside this set are marked as background. From each grid point $y_m$, $m \notin \mathcal{S}$, a pointer can be established that points to a dummy state that can represent background noise.

Regarding the step of block 124, for all grid points $y_m$, $m \notin \mathcal{S}$, consider all the neighboring grid points $p_1,\ldots,p_{n_m}$, which may be defined as the set of all grid points contained in the box $$\bigcap_{j=1}^{2}\{x : y_{m_j}-\Delta_j \leq x_j \leq y_{m_j}+\Delta_j\}$$

Letting $p \in \{p_1,\ldots,p_{n_m}\}$ such that $\hat{f}(p)=\max_{k=1,\ldots,n_m}\hat{f}(p_k)$, and splitting ties in an arbitrary manner, an association pointer can be established from $y_m$ to $p$ provided the following two conditions hold:

$\hat{f}(p) > \hat{f}(y_m)$ and $(\partial/\partial e)\hat{f}(y_m) > \lambda_m$, where $e=(p-y_m)/\|p-y_m\|$, $\|\cdot\|$.

$\|\cdot\|$ denotes Euclidean norm, and $(\partial/\partial e)\hat{f}(y_m)$ and $\lambda_m$ may be defined as follows:

$$\frac{\partial}{\partial e}\hat{f}(y_m) = \sum_{a=1}^{2} e_a \frac{\partial}{\partial y_{m_a}}\hat{f}(y_m),$$

$$\frac{\partial}{\partial y_{m_a}}\hat{f}(y_m) = \frac{1}{n}\sum_{l_1=-Z_1}^{Z_1}\sum_{l_2=-Z_2}^{Z_2} w_{m-l} \times \frac{-l_a\Delta_a}{h_a^2} \prod_{j=1}^{2} \frac{\phi(l_j\Delta_j/h_j)}{h_j},$$

$$\lambda_m = q(0.95^{1/\kappa})\sqrt{\hat{\Sigma}_m^2},$$

$$\kappa = \frac{\#\mathcal{S}\sum_{m \in \mathcal{S}} w_m}{n2\pi \prod_{j=1}^{2} h_j \sum_{m \in \mathcal{S}}\hat{f}(y_m)},$$

$$\hat{\Sigma}_m^2 = \frac{1}{n-1}\left(\sum_{a,b=1}^{2} e_a e_b \left[A - \frac{\partial}{\partial y_{m_a}}\hat{f}(y_m)\frac{\partial}{\partial y_{m_b}}\hat{f}(y_m)\right]\right),$$

$$A = \frac{1}{n}\sum_{l_1=-Z_1}^{Z_1}\sum_{l_2=-Z_2}^{Z_2} w_{m-l} \times \frac{l_a l_b \Delta_a \Delta_b}{h_a^2 h_b^2} \prod_{j=1}^{2} \frac{\phi^2(l_j\Delta_j/h_j)}{h_j^2}.$$

Here, $e_a$, $e_b$ denote the standard Euclidean basis vectors. $\hat{\Sigma}_m^2$ is an estimate of the variance of $(\partial/\partial e)\hat{f}(y_m)$ and $q(0.95^{1/\kappa})$ is the normal distribution critical value adjusted for multiple testing via $\kappa$. A is an estimate of $\partial/\partial y_{m_a}\hat{f}(y_m) (\partial/\partial y_{m_b})\hat{f}(y_m)$.

$q(x)$ denotes the 100·xth percentile of the standard normal distribution. All the sums can be computed with a FFT as above. Checking that the derivative at $y_m$ in the direction of p is significant, rather than just linking $y_m$ top, in order to prevent an accidental linking of different clusters. However, this approach may result in not being able to establish links near the maximum, where the density surface is flat. The step of block 126 may be carried out to merges such grid points.

The step of block 124 may be accomplished as follows. For all grid points $y_m$, $m \in \mathcal{J}$, in turn. If a pointer originates at $y_m$, then it will point to a different grid point, which itself may have a pointer originating from it. This succession of pointers is followed until one arrives at a grid point $y_z$ that either (a) $y_z$ does not have any pointer originating from it, or (b) $y_z$ has a pointer originating from it which points to a dummy state that represents a cluster or background noise.

In case (a) all the pointers visited in succession can be removed and new pointers originating from each grid point visited in succession can be established to the dummy state that represents the background noise, provided the following condition holds:

$$\hat{f}(y_z) < q(0.95^{1/K})\sqrt{\hat{\sigma}_z^2}.$$

Otherwise, provided there is a pointer into $y_z$, then a new pointer can be established that originates from $y_z$ and points to a newly established dummy state that represents a new cluster.

In case (b) no pointers need be removed or established.

The step of block 126 may be accomplished as follows. Let $\{y_{m(1)}, \ldots y_{m(k)}\}$ be the set of all grid points which have a pointer originating from them to a dummy state representing a cluster, enumerated such that $$\hat{f}(y_{m(1)}) \geq \ldots \geq \hat{f}(y_{m(k)}).$$

For $i=1, \ldots, k$ the following may be done:

Set $\mathcal{A} = \{m(i)\}$. Iterate the following loop until no more indices are added to $\mathcal{A}$:

(Begin Loop)

For each index $\mathfrak{a} \in \mathcal{A}$ in turn, the method may add all the indices p to $\mathcal{A}$ that satisfy (i) $y_p$ is a neighbor of $y_a$ as defined in Step 2,
(ii) no pointer originates from $y_p$,
(iii) $\hat{f}(y_p) + \hat{\sigma}_p \geq \hat{f}(y_{m(i)}) - \hat{\sigma}_{(i)}$
(End Loop)

Denote by $\mathcal{B}$ the set of indices of grid points which, e.g., satisfy the following two conditions. The grid point possesses a pointer originating to a dummy state representing a cluster, and the grid point has some $y_p$, $p \in \mathcal{A}$ as neighbor. If $\mathcal{B}$ is not empty, then the following may be done:

Define q by $\hat{f}(y_q) = \max_{r \in \mathcal{B}} \hat{f}(y_r)$, breaking ties arbitrarily.

Establish a pointer from each $y_p$, $p \in \mathcal{A} \setminus \{m(i)\}$, to $y_p$.

For each $r \in \mathcal{B}$, $r \neq q$, one may remove the pointer from $y_r$ to the dummy state representing a cluster and establish a new pointer from $y_r$ to $y_q$.

(End Loop Over i).

The step of block 128 may repeat the step of blocks 120-126 until there are no more additions or deletions of pointers to dummy states representing clusters.

According to aspects of an embodiment of the disclosed subject matter, the step of block 129 establish from each grid point that does not have a pointer originating from it, a pointer pointing to the dummy state that represents the background noise.

After the step of block 129 every grid point has a pointer originating from it. Following the succession of pointers leads to a dummy state which represents either background noise or a cluster, all grid points which are thus linked to the same dummy state pertain to the same cluster (or background noise). Cluster memberships of observations $x_i$ derive from the cluster memberships of the grid points as explained above.

2. Summarizing the Cell Population

Figure 7:
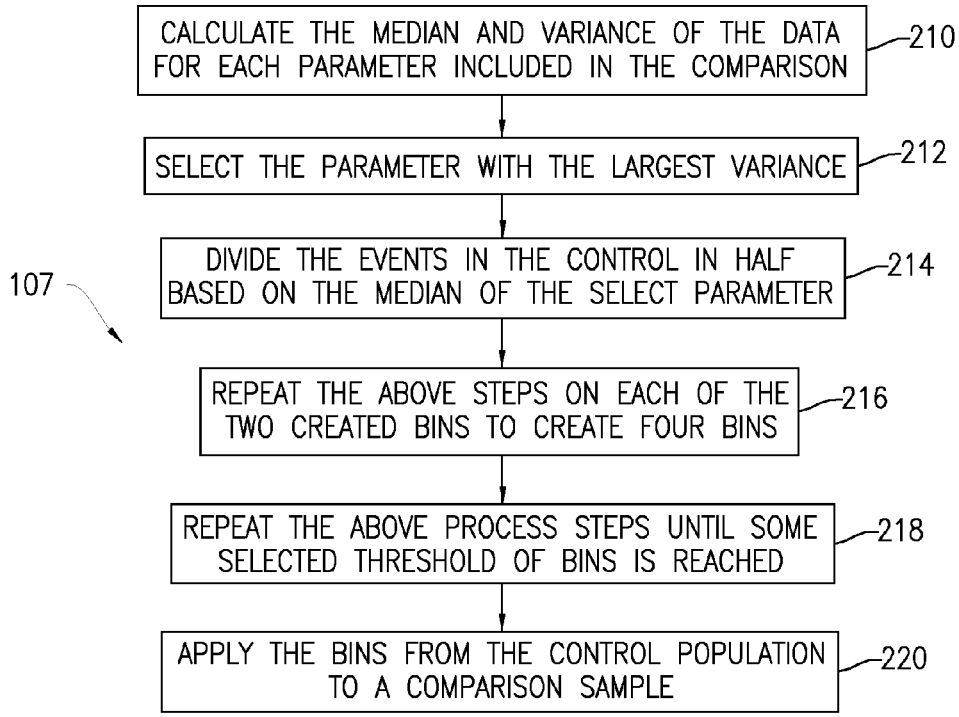
FIG. 7 shows in block diagram form the steps of a method for performing two of the steps in the method of FIG. 1.

Turning now to FIG. 7, according to another embodiment, there is shown in block diagram form a method 107 comprising the steps for performing the summarizing step of block 106 and the binning step of block 108 of FIG. 1, which may comprises utilizing an adaptive binning algorithm.

In order to carry out a Probability Binning Comparison (PBC), multivariate data must first be divided into bins, e.g., containing the same number of events. Thus, when binning, as an example, 10,000 events into 100 bins, each bin must contain 100 events. This necessitates that the bins are of different sizes. According to aspects of an embodiment of the disclosed subject matter the apparatus and method may successively divide a multivariate dataset into bins such that each bin has the same number of events, such as is illustrated in FIG. 7. The apparatus and method 107 begins in block 210 of FIG. 7 by calculating the median and variance of all of the data, for each of the parameters included in the comparison. It can then chose the parameter with the largest variance in block 212, and divide the events in half based on the median value of that parameter in block 214. By choosing the parameter with the largest variance, the method can be weighted towards assigning distinct clusters of events into distinct bins (or sets of bins).

The apparatus and method 107 can then repeats the process on each of the two newly-defined subsets, again determining the median and variance of all parameters of each subset, as indicated in block 216 of FIG. 7. This two-fold division process can continue until some specific threshold is met, as indicated in block 218. The result is, e.g., a series of n-dimensional hyper-rectangular bins. When the original control sample is separated into these bins, each bin has roughly the same number of events. Therefore, when selecting an event at random from the control population, there is an equal probability that it will fall into any given bin.

Figure 8:
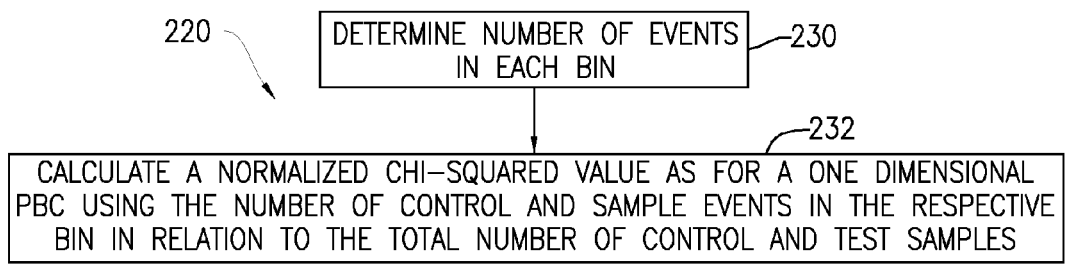
FIG. 8 shows in block diagram form the steps of a method for performing one of the steps of the method of FIG. 7.

The bins defined by the control population may then be applied to a comparison sample, as indicated in block 220 of FIG. 7. As indicated in block 230 of FIG. 8, the number of events falling within each bin are determined, and, in block 232 the normalized chi-squared value $\chi'^2$ can be calculated exactly as for the one-dimensional PBC, namely:

$$\chi'^2 = \sum_{i=1}^{\#bins} \frac{(c_i^n - s_i^n)^2}{(c_i^n + s_i^n)}$$

$$c_i^n = \frac{c_i}{E^c} \text{ and } s_i^n = \frac{s_i}{E^s}$$

given that $c_i$ and $s_i$ are the number of control and test sample events falling into bin i, and $E^c$ and $E^s$ are the total number of events in the control and test samples. Theoretically, $\chi'^2$ can range in values from a minimum of zero to a maximum of two.

A metric based on $\chi'^2$ can be derived empirically. This metric is analogous to a t-score, i.e., a value of zero indicates no statistical significance; a value of one indicates that the $\chi'^2$ is one standard deviation above the minimum significant value.

The minimum significant normalized chi-squared value $\overline{\chi}'^2$ and the associated standard deviation for this minimum chi-square based on the number of bins B used in the comparison, and the event count E (where E is the minimum of the number of events in the control sample ($E^c$) or the test sample ($E^s$):

$$\overline{\chi}'^2 = \frac{B}{E}$$

$$\sigma_{\chi'^2} = \frac{\sqrt{B}}{E}$$

As for the univariate comparison, we define the metric $T(\chi)$ as:

$$T(\chi) = \max\left(0, \frac{(\chi_m'^2 - \overline{\chi}'^2)}{\sigma_x'^2}\right)$$

A parameter to this apparatus and method may be the number of bins into which the control sample is to be divided. It is apparent from the above equations (since $\overline{\chi}'^2$ has a maximum value of two) that the number of bins should be kept low enough that the minimum significant value $\overline{\chi}'^2$ does not become so large as to preclude assigning statistical significance to any distribution. On the other hand, the number of bins should be maximized so as to most easily detect small changes in a distribution (i.e., if the entire change in a distribution were to occur within a single bin, then the statistic would not change). Thus, the effectiveness of the metric for detecting subtle changes (e.g., in terms of fluorescence intensity) may be limited by using small numbers of bins.

Unlike the case for univariate comparisons, the number of bins can quickly become limiting for this statistic (depending on the number of events collected and the number of parameters compared). The maximum reasonable number of bins is roughly 10% of the event count (leading to a minimum of about 10 events per bin; when using more bins, the number of events per bin is smaller, and the variance associated with each bin can increase dramatically). Thus for a 30,000 event collection, a maximum number of bins could be selected to be 3,000. This might be too many for univariate comparison where the limitation is the number of channels in the histogram that contain events (typically under 1024)). However, considering the case in which a comparison of all five parameters of a 3-color sample (including the two scatter parameters) is performed, three-thousand bins in five-dimensional space could mean that each parameter has been divided into approximately five divisions (on average) (i.e., $5^5$~3000).

The ability of the statistic to detect differences in distributions may be limited by the dimensions of the bin. The metric may be relatively insensitive to subtle changes in distribution with bins that span an average of $\frac{1}{5}^{th}$ of the range of each parameter (although the bins could be much smaller in areas with many events).

However, this limitation can be overcome by reducing the number of parameters in the comparison at a cost of losing the information provided by those parameters. In the above example, using only 4 parameters, each could be divided on average 7.5 times; comparing 3 parameters, each would be divided over 14 times ($14^3$~3,000).

If all five parameters are needed in the comparison, then more events may need to be collected in order to distinguish subtle variations in the distributions. It may be necessary to use a strategy of performing comparisons using different subsets of parameters in order to identify those which provide the least discriminating power. The final comparison could then be performed using as many useful parameters as possible given the limitations on the number of events collected.

The method and apparatus according to aspects of the disclosed subject matter can divide parameters with greater variance (more information) more frequently than parameters with low variance. Thus, in the example above, while the average number of divisions for a parameter may only be five, it is possible that (if the cells were lymphocytes) the two scatter channels may only be divided two or three times, leaving several additional divisions for the fluorescence parameters. Some knowledge of the expected outcome can provide an indication to the user of an appropriate number of events that need to be collected in order to achieve the desired level of detection.

In comparing multiple samples against each other, it is sometimes not possible (or meaningful) to assign a single sample as the control sample, against which all others are to be compared. In such a case, the bins may be constructed on the concatenation of all test samples. Each sample is then measured against the combined dataset; thus, each sample is assigned a value that is the distance from the average of the samples. This process can mitigate the potential artifact introduced by selection of a sample as a control that is actually significantly different than the expected control samples. It also may be useful to designate a set of samples to be used as the control for binning purposes, rather than including potentially distant outliers. According to some embodiments, all samples in the original binning are included, and the distances computed. After this, those samples which are most distinct can be removed from the set used as a control, and the statistic is recomputed.

According to some embodiments, the binning method 107 as illustrated in FIG. 7 may include the steps of beginning by calculating the variance for all of the data for each of the parameters included in the analysis as indicated in block 210. The method and apparatus may then chose the parameter/dimension with the largest variance, as indicated in block 212 and split the events into 2 bins along the median value in that dimension/parameter, as indicated in block 214, such that half of the events fall in each of the 2 resulting bins. The algorithm proceeds recursively on each of the 2 resulting bins, choosing the dimension that maximizes variance and splitting along the median, as indicated in block 216. This procedure continues until some threshold is met, as indicated in block 218. The result is a series of n-dimensional hyper-rectangular bins, each containing an equal number of events, which, e.g., may be applied to compare, such as, a control population to a sample population to be compared, as indicate in block 210, and as also illustrated in FIGS. 12A, 12B, and 12C.

Two alternatives to adaptive binning for summarizing multivariate distributions are (i) fixed width binning, and (ii) parametric distributions. Fixed width binning, the commonly used approach for histograms, creates bins of equal size containing varying density. Due to the sparsity of high dimensional space, this can result in most of the bins being empty and a relatively few number of bins containing all of the data. Adaptive binning has the favorable property of having a larger number of bins in the higher density regions and lower number of bins in the sparse regions. Summarizing the cluster by fitting a parametric distribution is another compact way of representing the data using just the mean and covariance for the case of a Gaussian distribution. Without being limited by theory, parametric approaches may not be suitable for the general case of summarizing cell populations since no theoretic model for the distribution of fluorescence molecules on cells exists, and empirical evidence has demonstrated a variety of irregular, convex distributions common to flow cytometry data.

3. Measuring a Shift in the Cell Population

Figure 9:
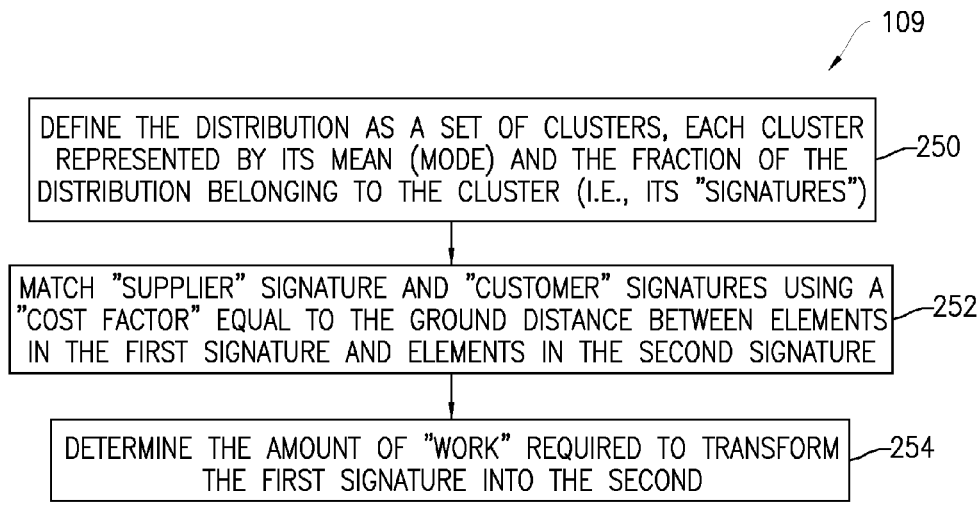
FIG. 9 shows in block diagram form the steps of a method for performing two of the steps of the method of FIG. 1.

According to another embodiment, the measuring step 110 of FIG. 1 and the determining step 112 may comprise a method and apparatus illustrated in block diagram form in FIG. 9, as steps in a method 109 for measuring the difference between two multivariate non-parametric distributions using Earth Mover's Distance ("EMD") algorithm.

The Earth Mover's Distance algorithm forms a possible method for evaluating dissimilarity between two multi-dimensional distributions in some feature space where a distance measure between single features ("ground distance") can be determined given. The EMD "lifts" this distance from individual features to full distributions.

Intuitively, given two distributions, one can be seen as a mass of earth properly spread in space, the other as a collection of holes in that same space. Then, the EMD measures the least amount of work needed to fill the holes with earth. Here, a unit of work corresponds to transporting a unit of earth by a unit of "ground distance."

As indicated in block 250 in FIG. 9, a distribution can be represented by a set of clusters where each cluster is represented by its means (or mode), and by the fraction of the distribution that belongs to that cluster. Such a representation is known as the "signature" of the distribution. The two signatures can have different sizes, for example, simple distributions have shorter signatures than complex ones.

Computing the EMD is based on a solution to the well-known "transportation problem" (see F. L. Hitchcock. The distribution of a product from several sources to numerous localities. *J. Math. Phys.*, 20:224-230, 1941). For example, suppose that several suppliers, each with a given amount of goods, are required to supply several consumers, each with a given limited capacity. For each supplier-customer pair, the cost of transporting a single unit of goods is given. The transportation problem is then to find a least-expensive flow of goods from the suppliers to the consumers that satisfies the consumers' demand. Matching signatures can be naturally cast as a transportation problem by defining one signature as the supplier and the other as the consumer, and by setting the cost for a supplier-consumer pair to equal the ground distance between an element in the first signature and an element in the second, as represented in block 252. Intuitively, the solution is then the minimum amount of "work" required to transform one signature into the other as indicated in block 254.

Figure 10:
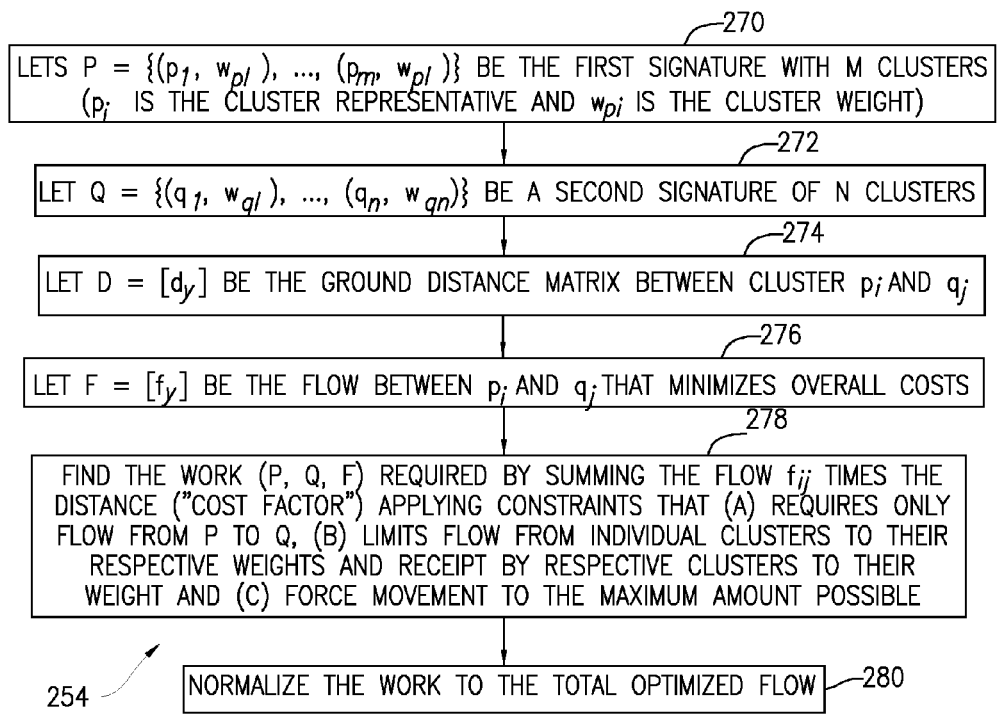
FIG. 10 shows in block diagram form further details of the steps of a method according to aspects of an embodiment of the disclosed subject matter.

This can be formalized as the following linear programming problem:

As indicated in block 270 of FIG. 10, which shows in block diagram form in more detail a method of performing the step 254 of FIG. 9, according to aspects of the disclosed subject matter, the method and apparatus disclosed may set $$P=\{(p_1, w_{p1}): \ldots :(p_m, w_{pm})\}$$

This can be the first signature within m clusters, where $p_i$ is the cluster representative and $w_{pi}$ is the weight of the cluster:

$$Q=\{(q_1, w_{q1}): \ldots :(q_n, w_{qn})\}$$

can be used as the second signature with n clusters, as indicated in block 272; and $$D=[d_{ij}]$$

as indicated in block 274, can be the ground distance matrix where $d_{ij}$ is the ground distance between cluster $p_i$ and $q_j$.

The method and apparatus may then find a flow $$F=[f_{ij}],$$

with $f_{ij}$ the flow between $p_i$ and $q_j$, that minimizes the overall cost, as indicated in block 276, i.e., $$\text{WORK}(P, Q, F) = \sum_{i=1}^{m} \sum_{j=1}^{n} f_{ij} d_{ij},$$

subject to the following constraints:

$$f_{ij} \geq 0 \quad 1 \leq i \leq m, 1 \leq j \leq n$$

$$\sum_{j=1}^{n} f_{ij} \leq w_{pi}, 1 \leq i \leq m$$

$$\sum_{i=1}^{m} f_{ij} \leq w_{qj} \quad 1 \leq j \leq n$$

$$\sum_{i=1}^{m} \sum_{j=1}^{n} f_{ij} = \min\left(\sum_{i=1}^{m} w_{pi}, \sum_{j=1}^{n} w_{qj}\right).$$

As indicated in block 278 of FIG. 10, in finding the minimized overall cost, WORK (P, Q, F), a first constraint can be applied to allow moving "supplies" from P to Q and not vice versa. The next two constraints can limit the amount of supplies that can be sent by the clusters in P to their weights, and the clusters in Q to receive no more supplies than their weights; and the last constraint can force the movement of the maximum amount of supplies possible. This amount is called the "total flow." Once the transportation problem is solved, and the optimal flow F has been found, the earth mover's distance is defined as the work normalized by the total flow as shown in block 280.

$$EMD(P, Q) = \frac{\sum_{i=1}^{m} \sum_{j=1}^{n} f_{ij} d_{ij}}{\sum_{i=1}^{m} \sum_{j=1}^{n} f_{ij}}.$$

The normalization factor can be introduced in order to avoid favoring smaller signatures in the case of partial matching.

The EMD has the following advantages in that EMD:

1) naturally extends the notion of a distance between single elements to that of a distance between sets, or distributions, of elements;

2) can be applied to the more general variable-size signatures, which subsume histograms (signatures are more compact, and the cost of moving "earth" reflects the notion of nearness properly, without the quantization problems of most other measures);

3) allows for partial matches in a very natural way, e.g., as may be advantageous for image retrieval and in order to deal with occlusions and clutter;

4) is a true metric if the ground distance is a metric and if the total weights of two signatures are equal, allowing the endowment of image spaces with a metric structure;

5) is bounded from below by the distance between the center of mass of the two signatures when the ground distance is induced by a norm, which can, through the use of this lower bound in retrieval systems, significantly reduce the number of EMD computations; and 6) matches the perceptual similarity better than other measures, when the ground distance is perceptually meaningful; for example, for color-based and texture-based image retrieval (see Rubner, Y., et al., A metric for distributions with applications to image databases. In *IEEE International Conference on Computer Vision*, pp. 59-66, January 1998).

The EMD is widely used in pattern recognition to compare generic summaries or surrogates of data records (signatures). A typical signature can consist of list pairs $((x_1,m_1), \ldots (x_n,m_n))$, where each $x_i$ is a certain "feature" (for example, color in an image, letter in a text, etc.), and $m_i$ is "mass" (how many times that feature occurs in the record). Alternatively, may be the centroid of a data cluster, and $m_i$ the number of entities in that cluster. To compare two such signatures with the EMD, one must define a distance between features, which can be interpreted as the cost of turning a unit mass of one feature into a unit mass of the other. The EMD between two signatures can then be a measure of the minimum cost of turning one of them into the other, which can then be used as a quantitative measure of the difference between the two.

According to some embodiments, the sample signature is defined as $\{(x_1, w_1), \ldots, (x_m, w_m)\}$ where $x_i$ (vector) are points in Euclidean space, and $w_i$ are the corresponding weights of the points. Work is the product of (a) the amount of weight being moved, and (b) the ground distance between the old and new location. The EMD between the two signatures can then be considered to be the sum of the work done by moving weights between each of the points from the source to the destination location.

Figure 11:
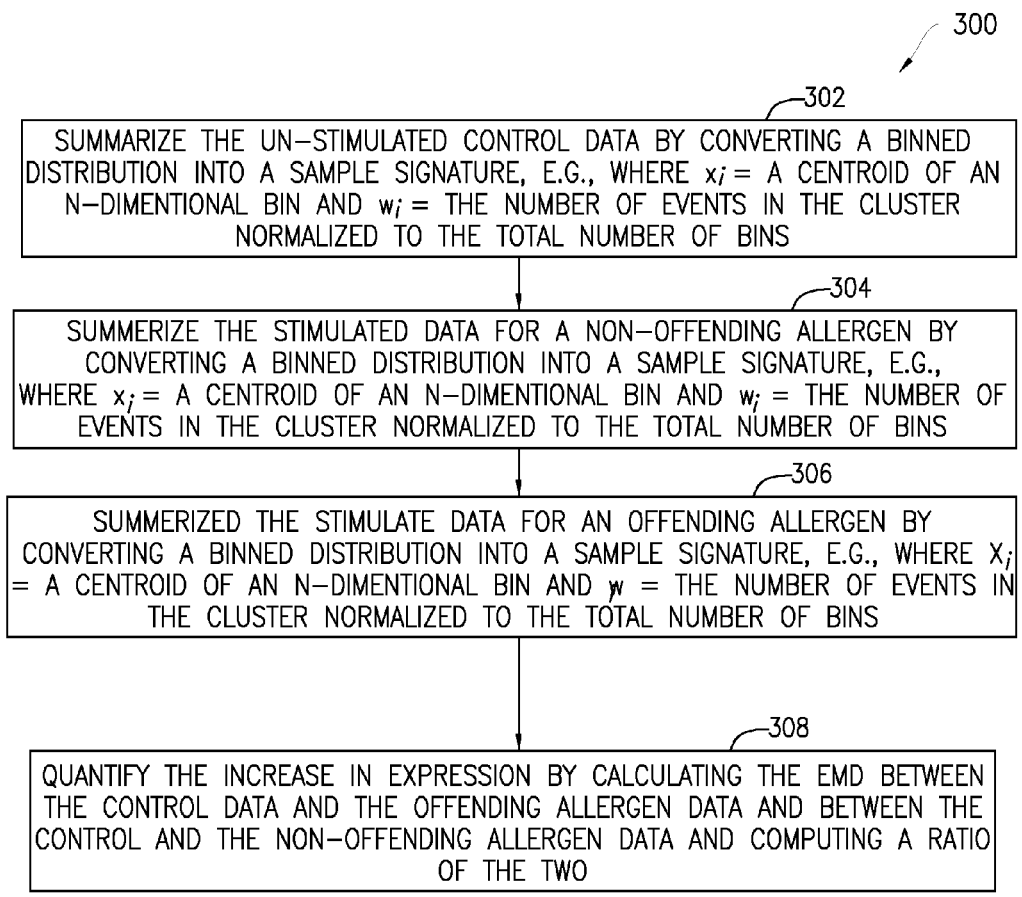
FIG. 11 shows in block diagram form the steps of a method according to aspects of an embodiment of the disclosed subject matter.

As indicated in block 302 of FIG. 11, a method 300—for quantifying a characteristic of certain distributed data Using the summarized data from the summarizing step of block 108 of FIG. 1, the binned distribution can be converted into a sample signature, such that $x_i$=the centroid of an n-dimensional hyper-rectangular bin and $w_i$=(number of events in the cluster/number of bins). The EMD then is computed between the two binned samples using Euclidean distance as the cost function.

For example, upon activation with nuts, two basophil surface markers, CD203c and CD63, are upregulated in patients with diagnosed allergies. According to aspects of the disclosed subject matter, the disclosed method and apparatus can quantify this increase in expression after stimulation to differentiate an allergic response. As illustrated in FIG. 11. for each patient sample and healthy control (n=10), the EMD can then be calculated, as indicated in block 308, between the unstimulated control (block 302) and samples stimulated with (1) non-offending allergen (block 304), and (2) offending allergen (block 306). The EMD fold change can be computed as a ratio of the offending/non-offending response. Using the fold change, a threshold can be defined, such as, at 2.5 to differentiate an allergic response with high sensitivity (100%) and specificity (86%).

EXAMPLES

The following examples are put forth so as to provide those of ordinary skill in the art with a disclosure and description of how to make and use the presently disclosed subject matter, and are not intended to limit the scope of what the inventors regard as the subject matter of the appended claims nor are they intended to represent that the examples below are all or the only examples that could be performed. Efforts have been made to ensure accuracy with respect to numbers used (e.g., amounts, temperatures, etc.) but the reader should account for some experimental errors and deviations.

Example 1

Method for Quantitative Comparison of Flow Cytometry Samples

First, Density-Based Merging (DBM) is used to assign individual cells to clusters based on measurements in two channels: a dump channel containing markers for cells that are to be removed from the analysis (such as CD3, CD16, CD19, CD66b, HLADR) and CD123, a marker on the surface of mature basophils). DBM delineates clusters of data using the contours of high-density regions, the same rationale underlying manual gating. Unlike many clustering algorithms, DBM does not require parameter tuning (e.g., number of clusters, modeled distribution of background) for individual datasets. The only parameter tuned for the study presented here is % outliers (Q), which determines what percent of the events do not get assigned to a cluster. If this value is set to 0, every event is assigned to a cluster. Basophils represent a very small number of the total cells collected from whole blood (<0.5%). Q was set accordingly at 0.5%. All other parameters are set according to statistical theory of density estimation (see, for example, Walther et al. Automatic Clustering of Flow Cytometry Data with Density-Based Merging. Advances in Bioinformatics (2009), vo. 2009, pp. 1-8; herein incorporated by reference in its entirety).

As illustrated by way of Example in FIGS. 12A, 12B, and 12C, respectively, 2-dimensional DBM clustering on the patient samples results in about 9 clusters per sample for the allergic patients and about 6 clusters per sample in the matched healthy controls. FIGS. 12A, 12B, and 12C represent one individual separated into three different data sets the unstimulated (FIG. 12A), non-offending allergen (FIG. 12B), and offending allergen (FIG. 12C), data distributions in two dimensions. The EMD algorithm can be utilized to quantify the changes, what clusters are changing from sample population to sample population for the individual and also to measure and quantify the changes within such clusters. The basophil cluster, indicated by the arrow, can be selected using a straightforward heuristic: the cluster with the highest median expression in the GD123 channel. (x-axis), and the lowest median expression in the dump channel (y-axis). This heuristic can be selected by reviewing the manual gating strategy used to analyze these data. The basophil-selection heuristic may not be robust to alterations of the stain set.

The selected basophil cluster contains between 200 and 1500 events. In order to efficiently calculate a distance metric between these clusters, the clusters can be summarized using the adaptive binning approach discussed above (see, for example, Roederer et al. Probability binning comparison: a metric for quantitating multivariate distribution differences. Cytometry (2001); herein incorporated by reference in its entirety). Calculating the metric on binned data can reduce the computational complexity of the distance metric with little loss in accuracy. Binning provides a simple, non-parametric method of summarizing multivariate distributions.

The binning algorithm, as noted above, illustrated in chart form in FIGS. 12A, 12B, and 12C, begins by calculating the variance for all of the data for each of the parameters included in the analysis. It chooses the dimension with the largest variance, and splits the events into 2 bins along the median value in that dimension, such that half of the events fill in each of the 2 resulting bins. The algorithm proceeds recursively on each of the 2 resulting bins, choosing the dimension that maximizes variance and splitting along the median. This procedure continues until some threshold is met. The result is a series of n-dimensional hyper-rectangular bins, each containing an equal number of events.

Third, upon activation with nuts, two basophil surface markers, CD203c and CD63, are upregulated in patients with diagnosed allergies. This increase in expression after stimulation is to be quantified to differentiate an allergic response. Earth Mover's Distance (EMD) (see, for example, Rubner et al. A metric for distributions with applications to image databases. Computer Vision, 1998. Sixth International Conference on DO1.10.1109/ICCV.1998.710701 (1998), pp. 59-66; herein incorporated by reference in its entirety) may be utilized for measuring the difference between two multivariate non-parametric data distributions. Given a function for calculating ground distance, EMD computes the minimal work required to transform one distribution into the other. EMD is computed between two sample signatures by minimizing the work required to move mass from one signature to the other. A sample signature is defined as $\{(x_i, w_i), \ldots, (xM, wM)\}$ where $x_i$ (vector) are points in Euclidean space, and $w_i$ are the corresponding weights of the points. Work is the product of (a) amount of weight being moved and (b) ground distance between the old and new location. The EMD between two signatures is the sum of the work done by moving weights between each of the points from the source to the destination location.

Using the summarized data from the step of block 108 of FIG. 1, the binned distribution is converted into a sample signature, such that $x_i$=the centroid of an n-dimensional hyper-rectangular bin and $w_i$=(number of events in the cluster/number of bins). Then, the EMD is computed between two binned samples using Euclidean distance as the cost function.

Turning now to FIGS. 12A, 12B, and 12C, an example is shown with independent samples and the question to be resolved is the correspondence between clusters. This illustrates a purpose of the use of the earth movers distance algorithm to do, e.g., population matching, i.e., cluster correspondence. The arrows in FIG. 12C represent corresponding clusters and result from cluster matching. A reason for wanting to find the correspondence is that one wishes to compare apples to apples, in this case, neutrophils between patients and not neutrophils to, e.g., lymphocytes. It will be understood that this is not the same case as where two parts of the same sample are compared for differences or similarities in clusters.

For each patient sample and healthy control (n=10), the EMD is calculated between the unstimulated control, panel 1, and samples stimulated with a (i) non-offending allergen, panel 2, and (ii) offending allergen, panel 3. Then, the EMD fold change is computed as a ratio of the offending/non-offending response. Using the fold change, a threshold is defined at 2.5 to differentiate an allergic response with high sensitivity (100%), and specificity (86%).

Figure 13A:
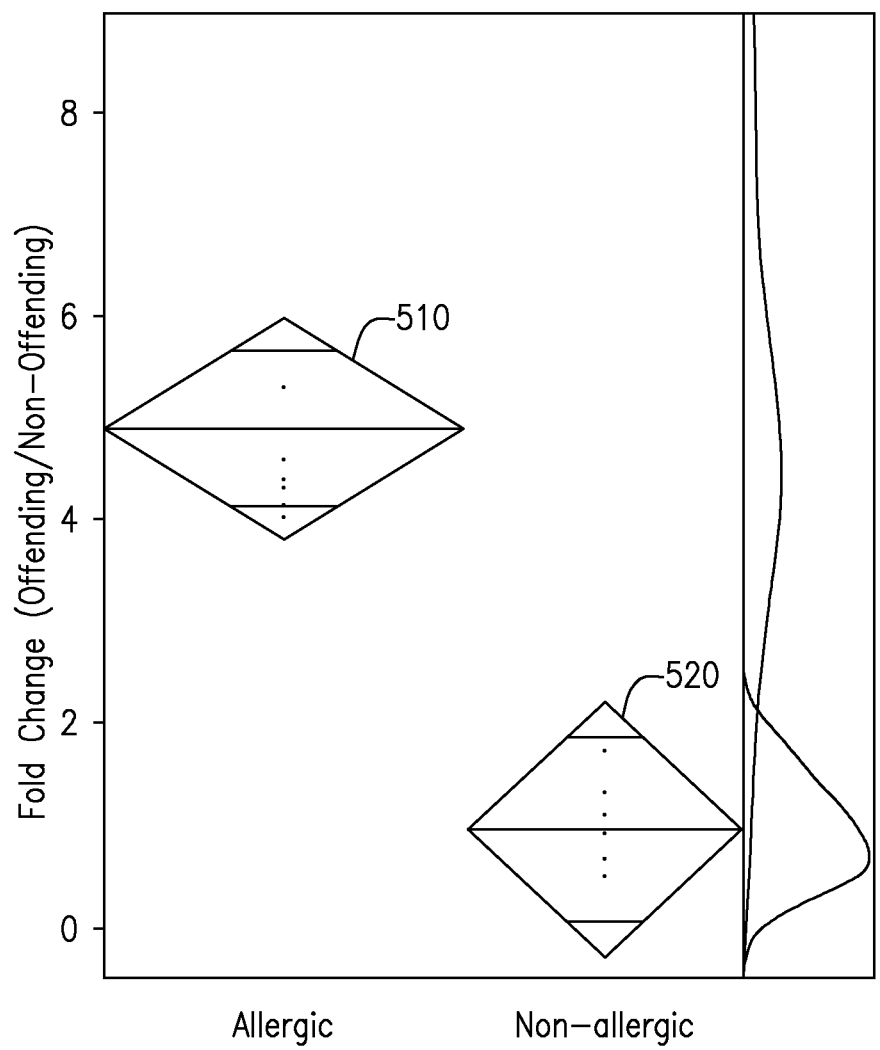
FIG. 13A shows a chart illustrating aspects of data comparison according to an embodiment of the disclosed subject matter.

FIG. 13A illustrates quantitative measurements of the differences in distributions illustrated for offending (allergic) and non-offending (non-allergic distributions in different patients, e.g., representing EMD population measurements for a parameter(s) in a dimension(s) for differing patients (dots 302 and 304). The allergic data distributions are shown to have a quantified patient-wise distribution having a mean at about 5 (normalized data) and a max and min at about 5.5 and 4, respectively (disregarding outliers). This is illustrated by the diamond 510 in FIG. 13A. The non-allergic patient-wise distribution has a mean at about 1 and a max and min at about 1.8 and 0 respectively, as illustrated in diamond 520 in FIG. 13A. This quantitatively shows a variation between non-allergic and allergic over a distribution of patients to be a five-fold change.

EMD has been used here to obtain two values, the unstimulated sample, i.e., not allergic and the stimulated sample, i.e., allergic. Each dot 302, 304 in FIG. 13A can be a representation of a ratio of these two values. The mean is different between nonallergic and allergic patient samples, with the noted five-fold increase in that value. Notably the nonallergic patients have a mean of about 1, i.e., no change, i.e., those patients are not allergic. FIG. 13A illustrates how the EMD algorithm can be utilized to measurement and demonstrate differences between individuals. The illustration of a group of different points together. Each dot 302, 304 represents one point. The means and the separation of the means are quantitative values comparing the two populations.

An EMD fold change can be calculated as a ratio:

$$\mathrm{EMD}(c,p)/\mathrm{EMD}(c,q)$$

where C is the unstimulated control, p is the sample stimulated with the offending allergen, and q is the sample stimulated with the non-offending allergen. The ratio can be utilized to normalize the shift in the response to the offending-allergen, by the response of the non-offending allergen.

The EMD fold change ratio of allergic patients (n=9, 1 not shown), points 302, versus nonallergic patients (n=6), points 304, is illustrated in FIG. 13A. Each point represents a single patient in the study. Allergic patients can be seen to display a 5-fold increase in the EMD fold change ratio on average, compared to a 1-fold increase in non-allergic patients.

FIG. 13A illustrates quantitative measurements of the differences in distributions illustrated for offending (allergic) and non-offending (non-allergic distributions in different patients, e.g., representing EMD population measurements for a parameter(s) in a dimension(s) for differing patients (dots 302 and 304. The allergic data distributions are shown to have a quantified patient-wise distribution having a mean at about 5 (normalized data) and a max and min at about 5.5 and 4, respectively (disregarding outliers). This is illustrated by the diamond 510 in FIG. 13A. The non-allergic patient-wise distribution has a mean at about 1 and a max and min at about 1.8 and 0 respectively, as illustrated in diamond 520 in FIG. 13A. This quantitatively shows a variation between non-allergic and allergic over a distribution of patients to be a five-fold change.

EMD has been used here to obtain two values, the unstimulated sample, i.e., not allergic and the stimulated sample, i.e., allergic. Each dot 302, 304 in FIG. 13A can be a representation of a ratio of these two values. The mean is different between nonallergic and allergic patient samples, with the noted five-fold increase in that value. Notably the nonallergic patients have a mean of about 1, i.e., no change, i.e., those patients are not allergic. FIG. 13A illustrates how the EMD algorithm can be utilized to measurement and demonstrate differences between individuals. The illustration of a group of different points together. Each dot 302,

304 represents one point. The means and the separation of the means are quantitative values comparing the two populations.

Figure 13B:
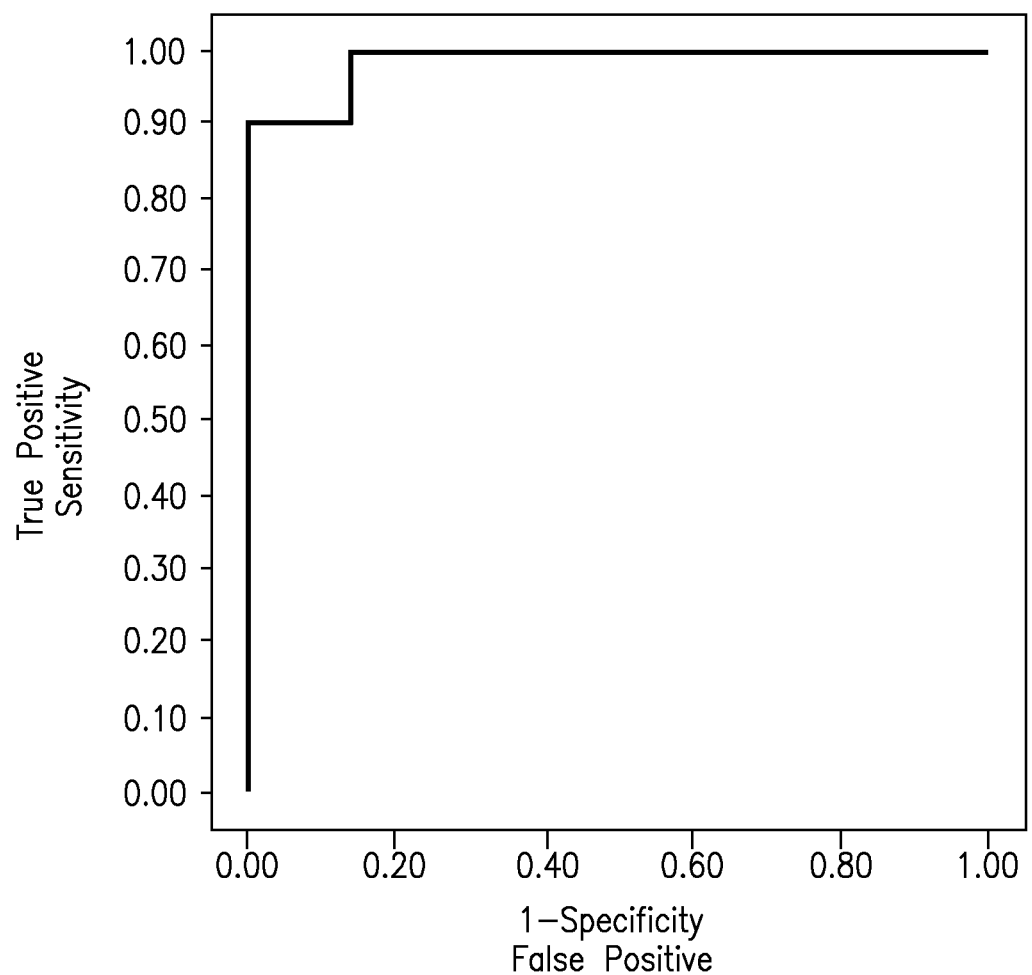
FIG. 13B shows a chart illustrating aspects of an embodiment of the disclosed subject matter.

FIG. 13B illustrates a receiver operating characteristic ("ROC") curve over a range of EMD fold change values (0-4). This can be used to measure the frequency of true positives (patients with diagnosed allergies that are predicted to have allergies) and false positives (patients with NO diagnosed allergies, that are predicted to have allergies) given different values of EMD fold change. The area under the curve is an indicator of a good of fit to the model. A model with an area under the curve=1 is a perfect fit, while a model with an area under the curve=0.5 has no predictive value.

It will be understood by those skilled in the art that the earth mover's distance ("EMD") algorithm is useful as a measurement for identifying differences between and among flow cytometry and other large data sets (or components of such large data sets). The approach, as discussed above, can be appropriate for multivariate data sets with continuous variables containing clusters, which, e.g., can be identified by density gradient variations and the like. Additionally, the approach is useful where the distributions have no known distributions individually or collectively, such as census data, data about what stores and what items are being patronized by shoppers in a shopping mall on any given day or period of time, and the like.

The foregoing disclosure relates to a very powerful tool for qualitative and quantitative analysis of populations of data, particularly multidimensional, especially higher levels of variables, multivariate populations. As noted, this is also especially true for populations of data samples that have no "normalized" shape in one or more dimensions. The principles of operation of the data analysis engine described in the present application are not limited to flow cytometry, though are very useful within that art to (a) to identify clusters of data sharing some parameter(s), such as, a common signature, and (b) what is changing within the cluster itself, e.g., in any dimension or plurality of dimensions. The former may be done by population division based on parameter differentiation, and the latter based on the way in which parameters are changing within a cluster.

As an example, as illustrated in FIGS. 12B and 12C, in the former application, the use of the EMD algorithm can identify clusters in the non-offending allergen, that are different from the unstimulated distribution, and in the offending allergen distribution that are different from either or both of the unstimulated and the non-offending allergen distributions. This is done, as noted above by parameterized division of the data into sets forming clusters. Beyond that, however, the EMD algorithm also serves to quantify differences in the data set within a given cluster, as is also discussed above.

It will be understood by those skilled in the art, therefore, that there are two applications of the disclosed subject matter which are independent of one another. In the one case the disclosed subject matter can identify a cluster that may be different in many dimensions from other data samples. The foregoing can be used to measure whether there are significant changes in any dimension, i.e., can a cluster be identified that has changed, e.g., in looking at the data for a given person, such as in FIGS. 12B and 12C, did something change with a changing parameter, i.e., is there something different between person A and person B and if there is, where is it occurring? How a particular cluster in the distribution changing between two conditions, and are they significant changes?

As such, the general principles can be applied to any characteristic associated with differences between two populations. In a specific example discussed in the present application, applying to flow cytometry, which relates to a multivariate distribution, the question to analyze is, is there any component significantly different from any other, e.g., for allergy response. The approach looks at a subset of cells (cluster) and measures response to a stimulus, and how different are the cells that express their response as an allergic reaction versus those cells that do not express an allergic reaction. This would show up as there being a significant difference between the two clusters within the overall distribution and/or between two overall distributions. The decision is more or less binary, is there a difference or not a difference. The approach can then subdivide that column for whatever the feature is that is not shown in the distribution and is a categorical variable.

In a second application of the EMD algorithm, the analysis can be of the changes in the cluster in the distribution, e.g., under different, and once having determined that the cluster is changing measuring by what it has changed in a given dimension. Generally the approach is to do a matching. For example, with two samples from two different patients which contain mixtures of lots of different types of cells, the clustering algorithm can identify the different clusters within the overall population. For example, 15 different clusters/populations may be identified, with respect to cells that represent populations or different types of cells from patient 1, and 12 different clusters/populations of cells for patient 2 when the same algorithm is applied. The matching relates to which of the corresponding clusters between the samples from patient A and patient B match, i.e., which basophils from A are most likely to match basophils from B. The EMD algorithm may be used as the criteria to do the matching.

Returning to FIGS. 12B and C illustrating an output of a clustering algorithm, in the case in which there is allergy, without the disclosed subject matter cluster matching would likely devolve to trying to visually discern different clusters are, e.g., colored or distributed differently, or the like. Colors may only delineate boundaries of clusters and may not carry over from panel, e.g., the unstimulated panel to the non-offending allergen panel, or from the non-offending allergen panel to the offending allergen panel. The use of the EMD algorithm solves this matching problem.

In one case what the clusters are may be known, i.e., these patient shows an increased amount of cluster 1 in several directions. Trying to compare person to person by looking at the amount that cluster movement in certain directions along different axes, etc., is very difficult. It is hard to determine how to align/match from individual to individual. The disclosed subject matter can be availed of to find which clusters match, such as by enabling one to standardize data where measurement variables are indeterminate or essentially not there at all.

In matching clusters one can be looking at clusters in the data, e.g., if looking at two populations, male and female, one can look at variables within those populations, what stores/TV shows do they prefer and what products/advertisements do they prefer, etc. In the alternative application, asking where is the significant difference between clusters A and B, the data may be for people who have been shopping in stores, some male, some female.

The different sample populations may be characterized, e.g., some pay by credit card, some pay cash, some by debit card. Differences may be taken between those who shop during the day, those who shop only on weekends, etc., each potentially forming a cluster. Another example is census data, i.e., taking two groups of people and asking what is different, e.g., males, females, and then further asking which things are in that cluster, i.e., what is the identity of that cluster and what is the change that is happening, without the need to identify a cluster from the start. Another example could be Nielsen ratings, which could be boiled down to one number for someone in one category (satisfying one parameter) living in the North vs. someone in a second category, such as, living in the South. Thus, according to aspects of an embodiment of the disclosed subject matter one can take two distributions of whatever kind of data and ask where, with respect to which parameters, do these differ and then by what criteria. Statistics are not utilized, but rather geometry based on calculations of distance, i.e., the earth mover's distance.

The algorithm can then be used to determine what is the difference in shopping behavior within each such cluster. Looking, e.g., at visual representations of the data, such as in FIG. 12A, one cannot see the clustering, and particularly cannot see the differences within a cluster, e.g., because the data is multivariate and also, e.g., because it has no known distributional shape. EMD enables seeing what is going on inside the different clusters, after identifying the differing clusters. It can be used to recognizes how one cluster changes to both identify the cluster and what does change within the cluster.

In the flow cytometry example, one could take all cells and dispense 10,000 cells into the wells of plates, with, e.g., 5 stimulations on those cells and a resultant 5 different values by a different measure/variable, one could do an analysis using the EMD algorithm based on functional values of the cells and distribution in the flow. The measurements do not have to be of the same type. This frees the analysis from the bounds of consistent measurement, i.e., from a 2D way of thinking because there can clearly be clusters identified by 3-4, or even more, ways of differentiation. For example, basophils are making CD63 and CD203 (FIG. 12A, for example). A key number could be the sum of CD63 and CD203. Which is the higher does not matter. The objective is to look at those two changes and other dimensions and how that cluster changes in response to 2, 3, 4 or even more parameters. This is in effect a dedifferentiating of the data, e.g., regarding CD63 and CD203, with the objective to see how individuals can be shown to be different and quantifying the difference, such as by utilizing the EMD algorithm to measure distance in many dimensions.

As a general principle when comparing two data sample or other distributions; one usually thinks about two bell-shaped curves and applying statistics. According to aspects of embodiments of the disclosed subject matter, the problem is approached from a different perspective. That is, without knowledge of or need to know what the shape of the distribution is applying the EMD as discussed above. The actual distribution(s) could be anything other than a regular distribution, i.e., shape of the distribution does not matter. In one application the approach could be utilized to determine when a cluster is missing, e.g., a cancer cell.

It will be understood by those skilled in the art that the earth mover's distance ("EMD") algorithm is useful as a measurement for identifying differences between and among flow cytometry and other large data sets (or components of such large data sets). The approach, as discussed above, can be appropriate for multivariate data sets with continuous variables containing clusters, which, e.g., can be identified by density gradient variations and the like. Additionally, the approach is useful where the distributions have no known distributions individually or collectively, such as census data, data about what sores and what items are being patronized by shoppers in a shopping maul on any given day or period of time, and the like.

The foregoing disclosure relates to a very powerful tool for qualitative and quantitative analysis of populations of data, particularly multidimensional, especially higher levels of variables, multivariate populations. As noted, this is also especially true for populations of data samples that have no "normalized" shape in one or more dimensions. The principles of operation of the data analysis engine described in the present application are not limited to flow cytometry, though are very useful within that art to (a) to identify clusters of data sharing some parameter(s), such as, a common signature, and (b) what is changing within the cluster itself, e.g., in any dimension or plurality of dimensions. The former may be done by population division based on parameter differentiation, and the latter based on the way in which parameters are changing within a cluster.

As an example, as illustrated in FIG. 12B, in the former application, the use of the EMD algorithm can identify clusters in the non-offending allergen, that are different from the unstimulated distribution, and in the offending allergen distribution that are different from either or both of the unstimulated and the non-offending allergen distributions. This is done, as noted above by parameterized division of the data into sets forming clusters. Beyond that, however, the EMD algorithm also serves to quantify differences in the data set within a given cluster, as is also discussed above.

It will be understood by those skilled in the art, therefore, that there are two applications of the disclosed subject matter which are independent of one another. In the one case the disclosed subject matter can identify a cluster that may be different in many dimensions from other data samples. The foregoing can be used to measure whether there are significant changes in any dimension, i.e., can a cluster be identified that has changed e.g., in looking at the data for a given person, such as in FIGS. 12A. 12B, and 12C, did something change with a changing parameter, i.e., is there something different between person A and person B and if there is, where is it occuring?How a particular cluster in the distribution changing between two conditions, and are they significant changes?

As such, the general principles can be applied to any characteristic associated with differences between two populations. In a specific example discussed in the present application, applying to flow cytometry, which relates to a multivariate distribution, the question to analyze is, is there any component significantly different from any other, e.g., for allergy response. The approach looks at a subset of cells (cluster) and measures response to a stimulus, and how different are the cells that express their response as an allergic reaction versus those cells that do not express an allergic reaction. This would show up as there being a significant difference between the two clusters within the overall distribution and/or between two overall distributions. The decision is more or less binary, is there a difference or not a difference. The approach can then subdivide that column for whatever the feature is that is not shown in the distribution and is a categorical variable.

In a second application of the EMD algorithm, the analysis can be of the changes in the cluster in the distribution, e.g., under different parameters, and once having determined that the cluster is changing measuring by what it has changed in a given dimension. Generally the approach is to do a matching. For example, with two samples from two different patients which contain mixtures of lots of different types of cells, the clustering algorithm can identify the different clusters within the overall population. For example, 15 different clusters/populations may be identified, with respect to cells that represent populations or different types of cells from patient 1, and 12 different clusters/populations of cells for patient 2 when the same algorithm is applied. The matching relates to which of the corresponding clusters between the samples from patient A and patient B match, i.e., which basophils from A are most likely to match basophils from B. The EMD algorithm may be used as the criteria to do the matching.

As a general principle when comparing two data sample or other distributions, one usually thinks about two bell-shaped curves and applying statistics. According to aspects of embodiments of the disclosed subject matter, the problem is approached from a different perspective. That is, without knowledge of or need to know what the shape of the distribution is applying the EMD as discussed above. The actual distribution(s) could be anything other than a regular distribution, i.e., shape of the distribution does not matter. In one application the approach could be utilized to determine when a cluster is missing, e.g., a cancer cell.

While the presently disclosed subject matter has been described with reference to specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the described invention. All such modifications are intended to be within the scope of the claims appended hereto.

The invention claimed is:

1. A method for identifying by flow cytometry corresponding subpopulations of biological cells between one or more first samples and one or more second samples by matching a biological cell population of interest in a first distribution of biological cells in the one or more first samples to a corresponding biological cell population in a second distribution of biological cells in the one or more second samples and quantitatively measuring a difference between the first distribution and the second distribution using a computing system including one or more processors to identify the presence or absence of: cancer cells, cells that express their response as an allergic reaction, or both in the second distribution of biological cells from the one or more second samples, the method comprising:

(a) obtaining individual data sets corresponding to measurements of individual biological cells for the one or more first samples and the one or more second samples, the data sets comprising multivariate, multidimensional individual data sets provided by a flow cytometry sample separator from analysis of samples including populations of biological cells with each individual data set corresponding to measurements of a single biological cell;

(b) dividing, by the one or more processors, the individual data sets corresponding to measurements of individual biological cells in the first distribution into clusters, wherein the data sets are of a normalized or an un-normalized shape;

(c) identifying or receiving a user input identifying one or more clusters in the first distribution as corresponding to the biological cell population of interest;

(d) summarizing data in the first distribution, by the one or more processors, by determining a first signature of the first distribution, the first signature including: a cluster location feature representative of a position of the cluster, and a cluster weight feature corresponding to a fraction of the entire first distribution that belongs to the cluster for each cluster in the first distribution;

(e) dividing, by the one or more processors, individual data sets corresponding to measurements of individual biological cells in the second distribution into clusters;

(f) summarizing data in the second distribution, by the one or more processors, by determining a second signature of the second distribution, the second signature including: a cluster location feature representative of a position of the cluster, and a cluster weight feature corresponding to a fraction of the entire second distribution that belongs to the cluster for each cluster in the second distribution;

(g) determining, by the one or more processors, a distance between two clusters using a cluster location feature for a cluster in the first distribution and a cluster location feature for a cluster in the second distribution for each combination of a cluster in the first distribution and a cluster in the second distribution, which is a quantitative measure of the difference between a first signature or elements of the first signature and a second signature or elements of the second signature that does not rely information regarding a shape of first distribution or a shape of the second distribution;

(h) determining, by the one or more processors, a measurement of a work required to move the first signature to the second signature by applying an earth mover distance algorithm including determining the optimal flow between clusters in the first distribution and clusters in the second distribution, thereby providing a quantitative measurement of a difference between the first distribution and the second distribution;

(i) matching, by the one or more processors, the one or more clusters corresponding to the biological cells of interest in the first distribution to one or more clusters in the second distribution based on the application of the earth mover distance algorithm, thereby identifying corresponding subpopulations of biological cells between the one or more first samples and the one or more second samples; and (j) based on the matching, identifying presence or absence of: cancer cells, cells that express their response as an allergic reaction, or both in the second distribution of biological cells from the one or more second samples.

2. The method of claim 1, wherein the first signature comprises a plurality of M clusters and the second signature comprises a plurality of N clusters.

3. The method of claim 1, wherein determining the measurement of the work in (h) further comprises:

(i) determining a separation distance matrix D between a first cluster matrix element and a second cluster matrix element;

(ii) determining a flow F between the first cluster matrix element and the second cluster matrix element that minimizes the overall measurement indicative of the separation between the first signature or elements of the first signature, and a second signature or elements of the second signature; and (iii) using the flow F to find the work required to move the first cluster matrix element into the second cluster matrix element.

4. The method of claim 3, further comprising:
normalizing the work to the total optimized flow F.

5. The method of claim 1, wherein the individual data sets are divided into clusters corresponding to measurements of individual biological cells in the first distribution using density-based merging.

6. The method of claim 1, further comprising performing adaptive binning to determine the binning for (d).

7. The method of claim 1, wherein the one or more first samples are from a first subject and the one or more second samples are from a second subject different from the first subject.

8. The method of claim 1, wherein the one or more first samples and the one or more second samples are from the same subject, and wherein analysis of the one or more second samples using the flow cytometry sample separator occurred after or while the one or more second samples were exposed to an agent or a stimulus.

9. The method of claim 1, wherein the one or more first samples were obtained from a subject at a first time and the one or more second samples were obtained from the same subject at a second time different from the first time.

10. The method of claim 9, wherein the one or more second samples were obtained from the subject during or after the subject was exposed to an agent or stimulus.

11. The method of claim 1, further comprising determining that a biological cell population of interest in the first distribution of biological cells in the one or more first samples does not have a corresponding biological cell population of interest in the second distribution of biological cells in the one or more second samples.

12. The method of claim 11, wherein the biological cell population of interest in the first distribution of biological cells in the one or more first samples that does not have a corresponding biological cell population of interest in the second distribution of biological cells in the one or more second samples comprises cancer cells.

13. An apparatus comprising a computing system including one or more processors and storage storing instructions that, when executed by the one or more processors, cause the computing system to carry out a method for identifying by flow cytometry corresponding subpopulations of biological cells between one or more first samples and one or more second samples by matching a biological cell population of interest in a first distribution of biological cells in the one or more first samples to a corresponding biological cell population in a second distribution of biological cells in the one or more second samples and quantitatively measuring a difference between the first distribution and the second distribution to identify the presence or absence of: cancer cells, cells that express their response as an allergic reaction, or both in the second distribution of biological cells from the one or more second samples, the method including:

(a) accessing individual data sets corresponding to measurements of individual biological cells for the one or more first samples and the one or more second samples, the data sets comprising multivariate, multidimensional individual data sets provided by a flow cytometry sample separator from analysis of samples including populations of biological cells with each individual data set corresponding to measurements of a single biological cell;

(b) dividing the individual data sets corresponding to measurements of individual biological cells in the first distribution into clusters, wherein the data sets are of a normalized or an un-normalized shape;

(c) identifying or receiving a user input identifying one or more clusters in the first distribution as corresponding to the biological cell population of interest;

(d) summarizing data in the first distribution by determining a first signature of the first distribution, the first signature including: a cluster location feature representative of a position of the cluster, and a cluster weight feature corresponding to a fraction of the entire first distribution that belongs to the cluster for each cluster in the first distribution;

(e) dividing individual data sets corresponding to measurements of individual biological cells in the second distribution into clusters;

(f) summarizing data in the second distribution by determining a second signature of the second distribution, the second signature including: a cluster location feature representative of a position of the cluster, and a cluster weight feature corresponding to a fraction of the entire second distribution that belongs to the cluster for each cluster in the second distribution;

(g) determining a distance between two clusters using a cluster location feature for a cluster in the first distribution and a cluster location feature for a cluster in the second distribution for each combination of a cluster in the first distribution and a cluster in the second distribution, which is a quantitative measure of the difference between a first signature or elements of the first signature and a second signature or elements of the second signature that does not rely information regarding a shape of first distribution or a shape of the second distribution;

(h) determining a measurement of a work required to move the first signature to the second signature by applying an earth mover distance algorithm including determining the optimal flow between clusters in the first distribution and clusters in the second distribution, thereby providing a quantitative measurement of a difference between the first distribution and the second distribution;

(i) matching the one or more clusters corresponding to the biological cells of interest in the first distribution to one or more clusters in the second distribution based on the application of the earth mover distance algorithm, thereby identifying corresponding subpopulations of biological cells between the one or more first samples and the one or more second samples; and (j) based on the matching, identifying presence or absence of: cancer cells, cells that express their response as an allergic reaction, or both in the second distribution of biological cells from the one or more second samples.

14. The apparatus of claim 13, wherein the first signature comprises a plurality of M clusters and the second signature comprises a plurality of N clusters.

15. The apparatus of claim 13, wherein determining the measurement of the work in (h) comprises:

(i) determining a separation distance matrix D between a first cluster matrix element and a second cluster matrix element;

(ii) determining a flow F between the first cluster matrix element and the second cluster matrix element that minimizes the overall measurement indicative of the separation between the first signature or elements of the first signature and the second signature or elements of the second signature; and (iii) using the flow F to find the work to move the first cluster matrix element into the second cluster matrix element.

16. The apparatus of claim 15, wherein determining the measurement of the work further comprises normalizing the work to the total optimized flow F.

17. The apparatus of claim 13, wherein the individual data sets are divided into clusters corresponding to measurements of individual biological cells in the first distribution using density-based merging.

18. The apparatus of claim 13, wherein the method carried out by the computing system further comprises performing adaptive binning to determine the binning for (d).

19. The apparatus of claim 13, wherein the one or more first samples are from a first subject and the one or more second samples are from a second subject different from the first subject.

20. The apparatus of claim 13, wherein the one or more first samples and the one or more second samples are from the same subject, and wherein analysis of the one or more second samples using the flow cytometry sample separator occurred after or while the one or more second samples were exposed to an agent or a stimulus.

21. The apparatus of claim 13, wherein the one or more first samples were obtained from a subject at a first time and the one or more second samples were obtained from the same subject at a second time different from the first time.

22. The apparatus of claim 21, wherein the one or more second samples were obtained from the subject during or after the subject was exposed to an agent or stimulus.

23. The apparatus of claim 22, wherein the method further comprises determining that a biological cell population of interest in the first distribution of biological cells in the one or more first samples does not have a corresponding biological cell population of interest in the second distribution of biological cells in the one or more second samples.

24. The apparatus of claim 23, wherein the biological cell population of interest in the first distribution of biological cells in the one or more first samples that does not have a corresponding biological cell population of interest in the second distribution of biological cells in the one or more second samples comprises cancer cells.

25. A non-transitory computer readable medium storing executable instructions that, when executed by a computing system, cause the computing system to perform a method for identifying by flow cytometry corresponding subpopulations of biological cells between one or more first samples and one or more second samples by matching a biological cell population of interest in a first distribution of biological cells in the one or more first samples to a corresponding biological cell population in a second distribution of biological cells in the one or more second samples and quantitatively measuring a difference between the first distribution and the second distribution to identify the presence or absence of: cancer cells, cells that express their response as an allergic reaction, or both in the second distribution of biological cells from the one or more second samples, the method including:

(a) accessing individual data sets corresponding to measurements of individual biological cells for the one or more first samples and the one or more second samples, the data sets comprising multivariate, multidimensional individual data sets provided by a flow cytometry sample separator from analysis of samples including populations of biological cells with each individual data set corresponding to measurements of a single biological cell;

(b) dividing the individual data sets corresponding to measurements of individual biological cells in the first distribution into clusters, wherein the data sets are of a normalized or an un-normalized shape;

(c) identifying or receiving a user input identifying one or more clusters in the first distribution as corresponding to the biological cell population of interest;

(d) summarizing data in the first distribution by determining a first signature of the first distribution, the first signature including: a cluster location feature representative of a position of the cluster, and a cluster weight feature corresponding to a fraction of the entire first distribution that belongs to the cluster for each cluster in the first distribution;

(e) dividing individual data sets corresponding to measurements of individual biological cells in the second distribution into clusters;

(f) summarizing data in the second distribution by determining a second signature of the second distribution, the second signature including: a cluster location feature representative of a position of the cluster, and a cluster weight feature corresponding to a fraction of the entire second distribution that belongs to the cluster for each cluster in the second distribution;

(g) determining a distance between two clusters using a cluster location feature for a cluster in the first distribution and a cluster location feature for a cluster in the second distribution for each combination of a cluster in the first distribution and a cluster in the second distribution, which is a quantitative measure of the difference between a first signature or elements of the first signature and a second signature or elements of the second signature that does not rely information regarding a shape of first distribution or a shape of the second distribution;

(h) determining a measurement of a work required to move the first signature to the second signature by applying an earth mover distance algorithm including determining the optimal flow between clusters in the first distribution and clusters in the second distribution, thereby providing a quantitative measurement of a difference between the first distribution and the second distribution;

(i) matching the one or more clusters corresponding to the biological cells of interest in the first distribution to one or more clusters in the second distribution based on the application of the earth mover distance algorithm, thereby identifying corresponding subpopulations of biological cells between the one or more first samples and the one or more second samples; and (j) based on the matching, identifying presence or absence of: cancer cells, cells that express their response as an allergic reaction, or both in the second distribution of biological cells from the one or more second samples.

26. The non-transitory computer readable medium of claim 25, wherein the first signature comprises a plurality of M clusters and the second signature comprises a plurality of N clusters.

27. The non-transitory computer readable medium of claim 25, wherein determining the measurement of the work in (h) comprises:

determining a separation distance matrix D between a first cluster matrix element and a second cluster matrix element;

determining a flow F between the first cluster matrix element and the second cluster matrix element that minimizes the overall measurement indicative of the separation between the first signature or elements of the first signature and the second signature or elements of the second signature; and using the flow F to find the work to move the first cluster matrix element into the second cluster matrix element.

28. The non-transitory computer readable medium of claim 27, further comprising:
normalizing the work to the total optimized flow F.

29. The non-transitory computer readable medium of claim 25, wherein the individual data sets are divided into clusters corresponding to measurements of individual biological cells in the first distribution using density-based merging.

30. The non-transitory computer readable medium of claim 25, wherein the method carried out by the computing system further comprises performing adaptive binning to determine the binning for (d).

31. The non-transitory computer readable medium of claim 25, wherein the one or more first samples are from a first subject and the one or more second samples are from a second subject different from the first subject.

32. The non-transitory computer readable medium of claim 25, wherein the one or more first samples and the one or more second samples are from the same subject, and wherein analysis of the one or more second samples using the flow cytometry sample separator occurred after or while the one or more second samples were exposed to an agent or a stimulus.

33. The non-transitory computer readable medium of claim 25, wherein the one or more first samples were obtained from a subject at a first time and the one or more second samples were obtained from the same subject at a second time different from the first time.

34. The non-transitory computer readable medium of claim 33, wherein the one or more second samples were obtained from the subject during or after the subject was exposed to an agent or stimulus.

35. The non-transitory computer readable medium of claim 25, wherein the method further comprises determining that a cell population of interest in the first distribution of biological cells in the one or more first samples does not have a corresponding biological cell population of interest in the second distribution of biological cells in the one or more second samples.

36. The non-transitory computer readable medium of claim 35, wherein the biological cell population of interest in the first distribution of biological cells in the one or more first samples that does not have a corresponding biological cell population of interest in the second distribution of biological cells in the one or more second samples comprises cancer cells.

37. A multivariate, multi-dimensional sample distribution analyzer comprising a computing system including one or more processors, the computing system configured for identifying corresponding subpopulations of biological cells between one or more first samples and one or more second samples by matching a biological cell population of interest in a first distribution of biological cells in the one or more first samples to a corresponding biological cell population in a second distribution of biological cells in the one or more second samples and quantitatively measuring a difference between the first distribution and the second distribution and identifying the presence or absence of: cancer cells, cells that express their response as an allergic reaction, or both in the second distribution of biological cells from the one or more second samples, the identifying corresponding subpopulations of biological cells between the one or more first samples and the one or more second samples, and identifying the presence or absence of: cancer cells, cells that express their response as an allergic reaction, or both in the second distribution of biological cells from the one or more second samples including:

(a) accessing individual data sets corresponding to measurements of individual cells for the one or more first samples and the one or more second samples, the data sets comprising multivariate, multidimensional individual data sets provided by a flow cytometry sample separator from analysis of samples including populations of biological cells with each individual data set corresponding to measurements of a single cell;

(b) dividing, by the one or more processors, individual data sets corresponding to measurements of individual biological cells in the first distribution into clusters, wherein the data sets are of a normalized or an unnormalized shape;

(c) identifying or receiving a user input identifying one or more clusters in the first distribution as corresponding to the cell population of interest;

(d) summarizing data in the first distribution, by the one or more processors, by determining a first signature of the first distribution, the first signature including: a cluster location feature representative of a position of the cluster, and a cluster weight feature corresponding to a fraction of the entire first distribution that belongs to the cluster for each cluster in the first distribution;

(e) dividing, by the one or more processors, individual data sets corresponding to measurements of individual biological cells in the second distribution into clusters;

(f) summarizing data in the second distribution, by the one or more processors, by determining a second signature of the second distribution, the second signature including: a cluster location feature representative of a position of the cluster, and a cluster weight feature corresponding to a fraction of the entire second distribution that belongs to the cluster for each cluster in the second distribution;

(g) determining, by the one or more processors, a distance between two clusters using a cluster location feature for a cluster in the first distribution and a cluster location feature for a cluster in the second distribution for each combination of a cluster in the first distribution and a cluster in the second distribution, which is a quantitative measure of the difference between a first signature or elements of the first signature and a second signature or elements of the second signature that does not rely information regarding a shape of first distribution or a shape of the second distribution;

(h) determining, by the one or more processors, a measurement of a work required to move the first signature to the second signature by applying an earth mover distance algorithm including determining the optimal flow between clusters in the first distribution and clusters in the second distribution, thereby providing a quantitative measurement of a difference between the first distribution and the second distribution;

(i) matching by the one or more processors, the one or more clusters corresponding to the biological cells of interest in the first distribution to one or more clusters in the second distribution based on the application of the earth mover distance algorithm, thereby identifying corresponding subpopulations of biological cells between the one or more first samples and the one or more second samples; and (j) based on the matching, identifying presence or absence of: cancer cells, cells that express their response as an allergic reaction, or both in the second distribution of biological cells from the one or more second samples.

38. The multivariate, multi-dimensional sample distribution analyzer of claim 37, wherein the individual data sets are divided into clusters corresponding to measurements of individual biological cells in the first distribution using density-based merging.

39. The multivariate, multi-dimensional sample distribution analyzer of claim 37, wherein the binning for (d) is determined using adaptive binning.

* * * * *